(12) United States Patent
Bayer et al.

(10) Patent No.: US 11,599,984 B2
(45) Date of Patent: Mar. 7, 2023

(54) METHODS AND APPARATUS FOR DETECTING DEFECTS FOR POULTRY PIECE GRADING

(71) Applicant: Syscom Inc., Baltimore, MD (US)

(72) Inventors: Theodore F. Bayer, Austin, TX (US); Randall E. Wilcox, Orlando, FL (US)

(73) Assignee: Syscom, Inc., Baltimore, MD (US)

( * ) Notice: Subject to any disclaimer, the term of this patent is extended or adjusted under 35 U.S.C. 154(b) by 0 days.

(21) Appl. No.: 17/699,093

(22) Filed: Mar. 19, 2022

(65) Prior Publication Data
US 2022/0351362 A1    Nov. 3, 2022

Related U.S. Application Data

(60) Provisional application No. 63/181,914, filed on Apr. 29, 2021.

(51) Int. Cl.
| | |
|---|---|
| *G06T 7/00* | (2017.01) |
| *G06T 7/70* | (2017.01) |
| *H04N 5/235* | (2006.01) |
| *G06V 10/764* | (2022.01) |
| *G01N 33/12* | (2006.01) |
| *B07C 5/342* | (2006.01) |
| *A22C 21/00* | (2006.01) |
| *B08B 3/08* | (2006.01) |
| *H04N 5/247* | (2006.01) |

(52) U.S. Cl.
CPC ........ *G06T 7/0004* (2013.01); *A22C 21/0053* (2013.01); *B07C 5/342* (2013.01); *B07C 5/3422* (2013.01); *B08B 3/08* (2013.01); *G01N 33/12* (2013.01); *G06T 7/70* (2017.01); *G06V 10/764* (2022.01); *H04N 5/2352* (2013.01); *H04N 5/247* (2013.01); *G06T 2207/30128* (2013.01)

(58) Field of Classification Search
None
See application file for complete search history.

(56) References Cited

U.S. PATENT DOCUMENTS

| | | | | |
|---|---|---|---|---|
| 5,847,382 | A | * 12/1998 | Koch | ............... G01N 33/12 209/939 |
| 5,980,377 | A | 11/1999 | Zwanikken et al. | |
| 6,151,866 | A | * 11/2000 | Connell | ............. A22C 21/0053 209/657 |

(Continued)

FOREIGN PATENT DOCUMENTS

| | | |
|---|---|---|
| CA | 2437876 A1 | 8/2002 |
| CN | 110236090 A * | 9/2019 |

(Continued)

OTHER PUBLICATIONS

Invitation to Pay Additional Fees et al. dated Jul. 1, 2022 in corresponding PCT Application No. PCT/US2022/023268.

*Primary Examiner* — Stefan Gadomski
(74) *Attorney, Agent, or Firm* — Harness, Dickey & Pierce, P.L.C.

(57) ABSTRACT

A system and method of inspecting a chicken piece comprising generating an image for the chicken piece, identifying a defect type, a defect location and an area of each defect on the chicken piece based on the image, and grading the chicken piece into one of a plurality of grades based on the defect type and the area.

82 Claims, 25 Drawing Sheets

(56) References Cited

U.S. PATENT DOCUMENTS

| | | | |
|---|---|---|---|
| 6,587,575 B1 * | 7/2003 | Windham | A22B 5/007 382/110 |
| 6,898,482 B2 | 5/2005 | Thorvaldsson et al. | |
| 7,633,614 B2 | 12/2009 | Haughholt et al. | |
| 7,775,373 B2 | 8/2010 | Grundtvig et al. | |
| 7,828,639 B2 | 11/2010 | Nielsen | |
| 8,625,856 B2 | 1/2014 | Chao et al. | |
| 8,708,784 B2 | 4/2014 | Bakker | |
| 8,892,246 B2 | 11/2014 | Thorsson et al. | |
| 9,795,148 B2 | 10/2017 | Sigurdsson et al. | |
| 10,488,644 B2 | 11/2019 | Eshel et al. | |
| 10,593,007 B1 * | 3/2020 | Long | H04N 19/44 |
| 2003/0098409 A1 * | 5/2003 | Bond | A22C 21/00 209/939 |
| 2003/0098796 A1 * | 5/2003 | Bond | G01N 29/048 209/509 |
| 2004/0022426 A1 * | 2/2004 | Carbone, II | G06T 7/0004 382/141 |
| 2004/0077302 A1 * | 4/2004 | Nielsen | A22C 21/0053 452/177 |
| 2005/0226465 A1 * | 10/2005 | Fujita | G06T 7/0004 382/110 |
| 2006/0157388 A1 * | 7/2006 | Blaine | B26D 5/007 209/3.2 |
| 2006/0217051 A1 * | 9/2006 | Gerrits | B65G 47/70 452/53 |
| 2007/0111648 A1 * | 5/2007 | Martel | A22B 5/007 452/118 |
| 2008/0204733 A1 * | 8/2008 | Jones | G01N 33/12 356/237.1 |
| 2009/0080706 A1 * | 3/2009 | Tao | G06T 7/0004 382/110 |
| 2009/0170417 A1 * | 7/2009 | Janssen | A22C 21/0053 452/136 |
| 2009/0216368 A1 | 8/2009 | Thorsson | |
| 2009/0309960 A1 * | 12/2009 | Park | G01J 3/0272 348/61 |
| 2010/0029187 A1 * | 2/2010 | Haucke | A22C 17/008 452/184 |
| 2010/0140461 A1 * | 6/2010 | Sprigle | G01J 3/2823 250/226 |
| 2012/0247920 A1 * | 10/2012 | Peters | B65G 47/248 198/407 |
| 2016/0069743 A1 * | 3/2016 | McQuilkin | G01N 21/255 356/416 |
| 2017/0108855 A1 * | 4/2017 | Hocker | A22C 17/0006 |
| 2017/0205385 A1 * | 7/2017 | Prystupa | G01N 21/3563 |
| 2019/0116816 A1 * | 4/2019 | Dirac | A22C 17/008 |
| 2020/0060294 A1 | 2/2020 | Thoroddsen et al. | |
| 2020/0193587 A1 * | 6/2020 | Mairhofer | G01N 21/84 |
| 2020/0288731 A1 | 9/2020 | Hjalmarsson et al. | |
| 2021/0035276 A1 * | 2/2021 | Ago | G01N 21/9515 |
| 2021/0041378 A1 * | 2/2021 | Morton | G01N 23/10 |

FOREIGN PATENT DOCUMENTS

| | | | | |
|---|---|---|---|---|
| CN | 112385813 A | * | 2/2021 | |
| CN | 112568183 A | * | 3/2021 | |
| EP | 2777406 A1 | * | 9/2014 | A23P 1/084 |
| EP | 3716771 A1 | | 10/2020 | |
| JP | 2021050959 A | * | 4/2021 | |
| WO | WO-2005102063 A2 | * | 11/2005 | A22B 5/007 |
| WO | WO-2006129391 A1 | * | 12/2006 | B07C 5/3422 |
| WO | WO-2019039329 A1 | * | 2/2019 | |
| WO | WO-2019099345 A1 | * | 5/2019 | |
| WO | WO-2020064075 A1 | * | 4/2020 | A22B 5/007 |

\* cited by examiner

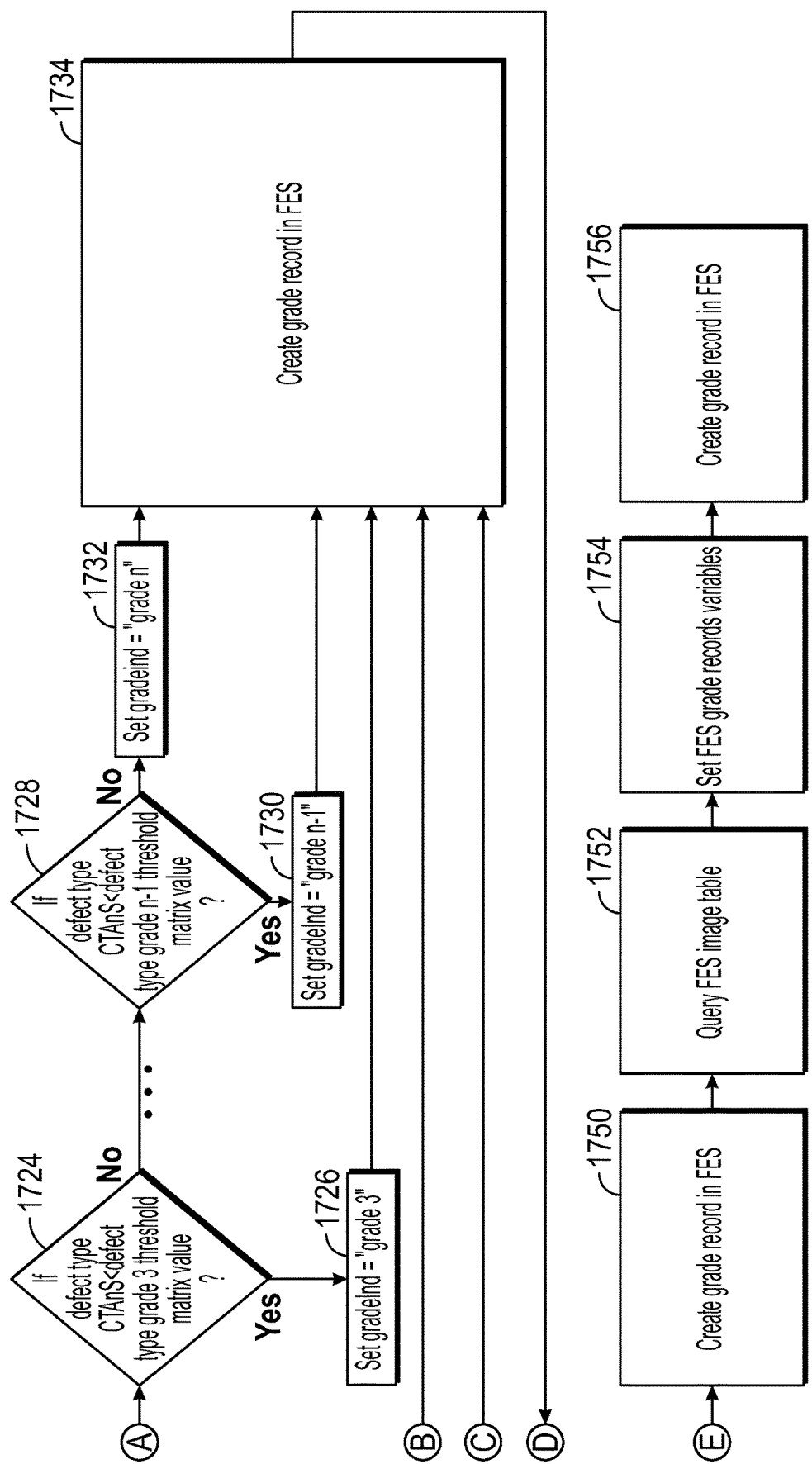

Grade Threshold Matrix — 1910

| Defect Type | Grade 1 | Grade 2 | Grade 3 | Grade 4 | ... | Grade n-1 | Grade n |
|---|---|---|---|---|---|---|---|
| Filament Edge | 136000 | 7,140.000 | 21630000 | 999999999 | | | |
| Filament Surface | 136000 | 7,140.000 | 21630000 | 999999999 | | | |
| Inflammation | 185 | 999999999 | | | | | |
| Rod | 203 | 999999999 | | | | | |
| Root | 95 | 999999999 | | | | | |

FIG. 19

Grade Bin Matrix — 2010

| Defect Type | Defect Grade Precedence | No Grade | Grade 1 | Grade 2 | Grade 3 | Grade 4 | ... | Grade n-1 | Grade n |
|---|---|---|---|---|---|---|---|---|---|
| Villi | 1 | | 0 | 1 | 2 | 3 | | N/A | N/A |
| Inflammation | 2 | | 0 | 4 | N/A | N/A | | N/A | N/A |
| Rod | 3 | | 0 | 4 | N/A | N/A | | N/A | N/A |
| Root | 4 | | 0 | 4 | N/A | N/A | | N/A | N/A |
| No Defect | | | | | | | | | |
| Reevaluate | | 5 | | | | | | | |
| Invalid | | 6 | | | | | | | |

FIG. 20

METHODS AND APPARATUS FOR DETECTING DEFECTS FOR POULTRY PIECE GRADING

CROSS-REFERENCE TO RELATED APPLICATION

This application claims the benefit of U.S. Provisional Application No. 63/181,914, filed on Apr. 29, 2021. The entire disclosure of the above application is incorporated herein by reference.

FIELD

The present disclosure relates generally to a method and system for inspecting an item and, more specifically, determining defects in a food item.

BACKGROUND

The statements in this section merely provide background information related to the present disclosure and may not constitute prior art.

Presently, the primary method of detecting visual defects on a piece of poultry, involves poultry processing line inspectors manually inspecting a piece of poultry in a batch on a table or while the piece moves down the processing line. Some defects are visible from the top view of a piece moving down the processing line, but others require picking up the piece and turning it over to view both sides or obtain a much closer view for small defects. With the targeted processing volumes of poultry processing lines, manual visual inspection requires many inspectors that are unable to inspect but only a percentage of pieces moving down the line. Therefore, defects may be missed.

SUMMARY

This section provides a general summary of the disclosure and is not a comprehensive disclosure of its full scope or all its features.

An automated inspection system and method for identifying defects on an item such as poultry pieces is set forth. The detecting system uses the combination of a semi-automatic continuously cleaned transparent conveyor belt allowing 360° piece image capture, an analytics pipeline leveraging image processing, deep learning image classification and object localization/detection technologies, and a customizable decision pipeline leveraging the defect features extracted by the analytic pipeline to grade and inform poultry piece human or automated remediation with visual imagery and/or structured information about the defects.

In accordance with some examples, a poultry piece is placed on a processing line conveyor belt either manually or from upstream processing. The pieces are spaced and are directed to the center of a belt and then transferred to a transparent belt before entering the analytics enclosure. The transparent belt will move continuously to carry pieces through the analytics enclosure for 360° image capture and then transferred back to a conventional belt exiting the enclosure. To maintain the visual transparency of the belt, a semi-automatic belt cleaning system removes carryback particulates by spraying/rinsing the belt continuously using peracetic acid solution and/or followed by an air knife to reduce bottom image capture visual disturbance from liquid remaining on the belt. Use of a transparent belt in this manner is novel in this industry. Transparent belts are used for back-lighting but viewing through the belt has heretofore not been employed.

Inside the enclosure there are two or more field of views for image capture. The fields of view capture images from the top of the belt with a camera/light or electromagnetic radiation (EM) array and from the bottom through the belt with a camera array/light array. Each FOV camera/lighting or EM array is triggered using a photo sensor trigger as the piece enters the FOV. As the piece enters the enclosure a photo sensor will trigger the image capture for each FOV.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method of inspecting a chicken piece. The method also includes generating an image for the chicken piece. The method also includes identifying a defect type, a defect location and an area of each defect on the chicken piece based on the image. The method also includes grading the chicken piece into one of a plurality of grades based on the defect type and the area. Other embodiments of this aspect include corresponding computer systems, apparatus, and computer programs recorded on one or more computer storage devices, each configured to perform the actions of the methods.

Implementations may include one or more of the following features. The method where generating the image may include generating the image from within an enclosure. Generating the image may include generating the image when the chicken piece enters a field of view of an image device. Generating the image may include generating a first image for a first side of the chicken piece and a second image for a second side of the chicken piece. Generating the image may include generating a first image for a first side of the chicken piece and generating a second image for a second side of the chicken piece through a transparent conveyor belt. Prior to generating a second image for the second side of the chicken piece through the transparent conveyor belt, cleaning the transparent belt. Generating the image may include generating a first image for a first side of the chicken piece, a second image for a second side of the chicken piece, a third image for the first side of the chicken piece and a fourth image for the second side of the chicken piece. Generating the image may include generating a first image for a first side of the chicken piece with a first image device using a first gain, a second image for a second side of the chicken piece with a second image device using a second gain, a third image for the first side of the chicken piece with a third image device using a third gain and a fourth image for the second side of the chicken piece with a fourth image device using a fourth gain, said first gain different than the third gain and the second gain is different than the fourth gain. Identifying the defect type, the defect location and the area of each defect on the chicken piece may include identifying the defect type, the defect location and the area of each defect on the chicken piece deep learning image classification and deep learning object detection. The method may include sorting the chicken piece in a sorting system based on the grade. The method may include communicating the chicken piece from a sorting system to a remediation system based on the grade. The method may include determining a piece type based on the image. The method may include sorting the piece in a sorting system based on the grade and piece type. The method may include displaying on a display the image and the defect location. Identifying the defect type may include determining areas of a plurality of defects and summing the areas. Identifying the defect type may include determining an area of a defect raised to an exponent. Identifying the defect type may include determining a filament or a cluster of filaments. Identifying the defect type may include determining at least one of a dermatitis, scabby, and gore. Identifying the defect type may include determining decolorization. Identifying the defect type may include determining rods or feathers. Identifying the defect type may include determining white roots or black roots. Identifying the defect type may include determining a matter of cut. Identifying the defect type is based on an adjustable threshold. Implementations of the described techniques may include hardware, a method or process, or computer software on a computer-accessible medium.

One general aspect includes an inspection system for inspecting an item. The inspection system also includes a conveyor belt for moving the item thereon. The system also includes a first image device generating a first image signal of the item from a first field of view. The system also includes a second image device generating a second image signal of the item from a second field of view. The system also includes an electromagnetic source disposed within the enclosure directing electromagnetic radiation to the first field of view and the second field of view. The system also includes a controller coupled to the first image device and the second image device generating a numerical identifier based on the first image signal and the second image signal. The system also includes a display displaying an indicator based on the numerical identifier. Other embodiments of this aspect include corresponding computer systems, apparatus, and computer programs recorded on one or more computer storage devices, each configured to perform the actions of the methods.

Implementations may include one or more of the following features. The inspection system may include an enclosure disposed around the first field of view and the second field of view. The conveyor may include a transparent conveyor belt and where first image device is disposed on a first side of the conveyor belt and the second image device is disposed on a second first side of the conveyor belt. The inspection system may include a cleaning system cleaning the transparent conveyor belt. The first field of view is aligned with the second field of view. The electromagnetic source may include a first portion disposed on a first side of the conveyor belt and a second portion disposed on a second side of the conveyor belt. The cleaning system may include an air knife and a bath. The electromagnetic source may include a visible light system. The inspection system may include a display device coupled to the controller, said display device generating an image of the item and display indicia identifying a surface defect. The first image device may include a first gain and the second image device may include a second gain different that the second gain. The second field of view is spaced apart from the first field of view. The controller generates the numerical identifier based on the first image signal, the second image signal, the third image signal and the fourth image signal. The second image device and the fourth image device are disposed on opposite sides of the conveyor belt as the first image device and the third image device, the first field is aligned with the second field of view and the third field of view is aligned with the fourth field of view. The inspection system may include a sorting system sorting the item based on the numerical identifier. The controller determines the numerical identifier by determining an area of a defect. The controller determines the numerical identifier by determining areas of a plurality of defects and summing the areas to form the numerical identifier. The controller determines the numerical identifier by determining an area of a defect raised to an exponent. The inspection system may include a user interface for changing the exponent. The item may include a poultry piece and where the numerical identifier may include a surface defect. The surface defect may include a filament and cluster of filaments. The surface defect may include at least one of a dermatitis, scabby, and gore. The surface defect may include decolorization. The surface defect may include rods or feathers. The surface defect may include white roots or black roots. The surface defect may include a matter of cut. The numerical identifier may include a grade of a plurality of grades. The grade corresponds to a plurality of thresholds adjustable using a user interface. Implementations of the described techniques may include hardware, a method or process, or computer software on a computer-accessible medium.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 17A-17B is a flowchart of the method for operating the multi-camera grade evaluation of FIGS. 15A-15B.

FIG. 19 is a representation of a grade threshold matrix.

FIG. 20 is a flowchart of a grade bin matrix.

DETAILED DESCRIPTION

Figure 1:
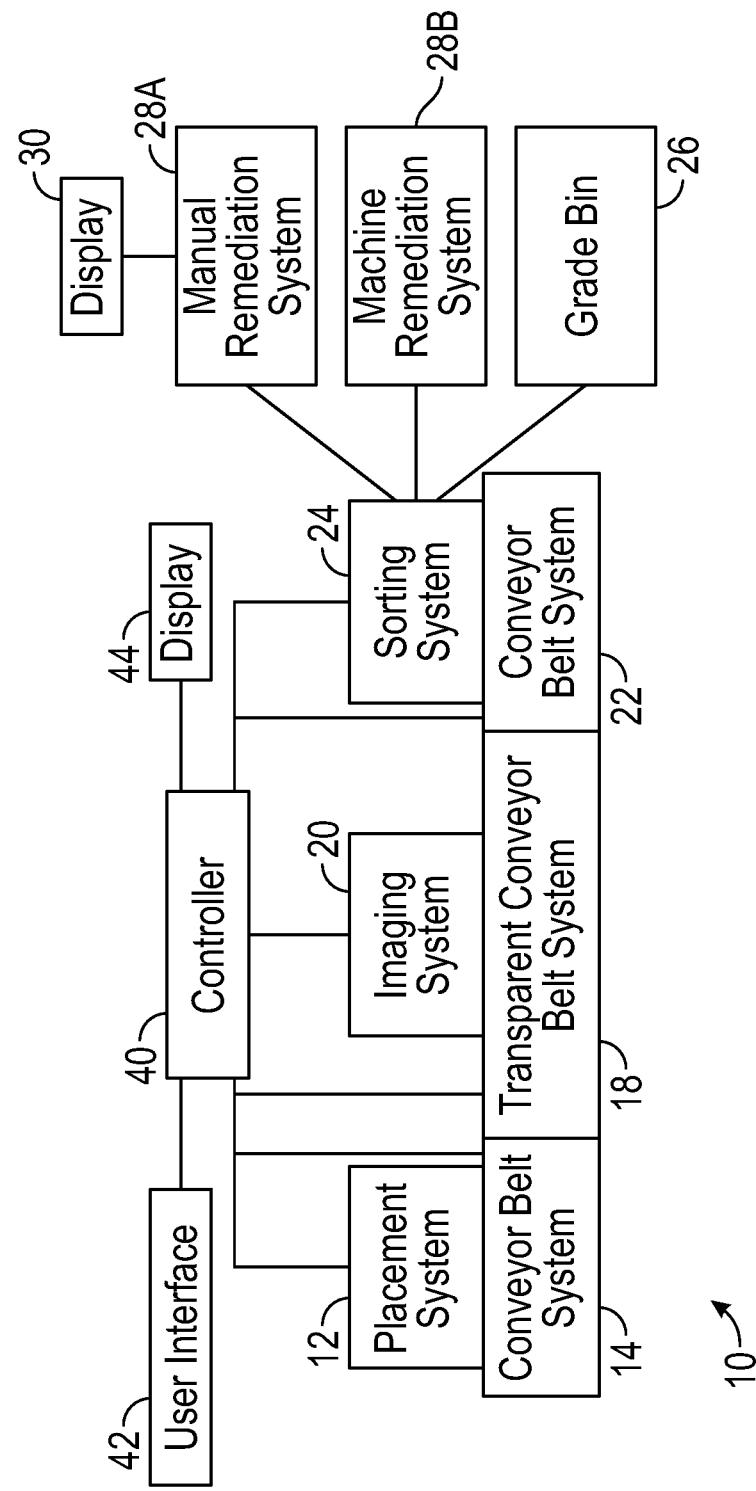
FIG. 1 is a level block diagrammatic view of the inspection system according to the present disclosure.

Example embodiments will now be described more fully with reference to the accompanying drawings.

The following description is merely exemplary in nature and is not intended to limit the present disclosure, application, or uses. For purposes of clarity, the same reference numbers will be used in the drawings to identify similar elements. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality. As used herein, the phrase at least one of A, B, and C should be construed to mean a logical (A or B or C), using a non-exclusive logical OR. Steps within a method may be executed in different order without altering the principles of the present disclosure. The following is described with respect to poultry pieces.

The system is constructed of components suitable for the harsh environment of food processing. In animal processing the environment is cold and cleaned often. Waterproof components or enclosures may be used to prevent damage and increase accuracy.

In the following description the word message is to identify an electronic signal comprising the specific data. Various servers and processors communicate with the electronic signals to perform the various methods.

Referring now to FIG. 1, an inspection system 10 is shown in a high level block diagrammatic form. The inspection system 10 has a placement system 12 that is used for placing pieces for inspection. In the present example, the inspection system 10 may be used for inspecting food such as poultry pieces. However, other types of pieces, including non-food pieces, may be inspected. The placement system 12 is used for placing the pieces onto a conveyor belt system 14. The placement system may be a human system for placing the pieces onto the conveyor belt system in an agreed upon manner. The placement system 12 may also be fully automated. That is, pieces may come in a container. In such a case, a robot or another type of device may position the pieces onto the conveyor belt system 14 from the container. In one example, a singulator positions the pieces with a predetermined spacing onto the conveyor belt system 14.

The conveyor belt system 14 may be various sizes and operate at various speeds depending upon the desired operating conditions and the types of pieces to be inspected. Regulatory bodies may also dictate line speed for certain types of pieces such as food pieces. The conveyor belt system 14 may be an opaque belt that forms an endless loop to provide the pieces to a transparent conveyor belt system 18 which convey the pieces to an imaging system 20.

The imaging system 20 is used for generating images of the pieces. Based upon the images from the imaging system 20, a conveyor belt system 22 receives the pieces and a sorting system 24 sorts the pieces into one or more grade bins 26 that have the pieces sorted therein or one or more remediation systems. The remediation system may be a manual remediation 28A or an automated remediation system 28B that is automatically operated as will be described in further detail below. Based upon the images from the imaging system 20, indicia such as the location of the defects to be remediated may be displayed on a display 30. That is, some of the remediation systems 28 may require manual processing by humans and others may be automated. In either case, the location of the defect provided from the imaging system will allow either a human or an automated system to correct the defect or defects on each piece.

A controller 40 is used to control the overall processing and inspecting of the pieces. The controller 40 is illustrated as a single component in FIG. 1. However, multiple controllers for controlling various portions of the system may be used. As will be described in more detail below, one or more programmable logic controllers (PLCs) and industrial personal computer (IPCs) may be used. The controller 40 may be microprocessor-based with various logic circuitry programmed to perform inspecting for a particular type of part. The controller 40 may be controlled through a user interface 42. The user interface 42 may be one or more of a switch, a dial, a button, a knob, a keypad, a keyboard, a microphone or a touch screen. The user interface 42 allows a user to configure the inspection system 10, such as configuring the conveyor belt speed, the batch, the type of pieces to expect, the grading system and the like. The user interface 42 also allows requesting numerical identifier data to be displayed such as the number of processed pieces, grading determinations, failures and remediation data.

The controller 40 may also be coupled to a display 44. The display 44 may display various control parameters, defect data, processing data and other processing parameters of the inspection system 10.

Figure 2:
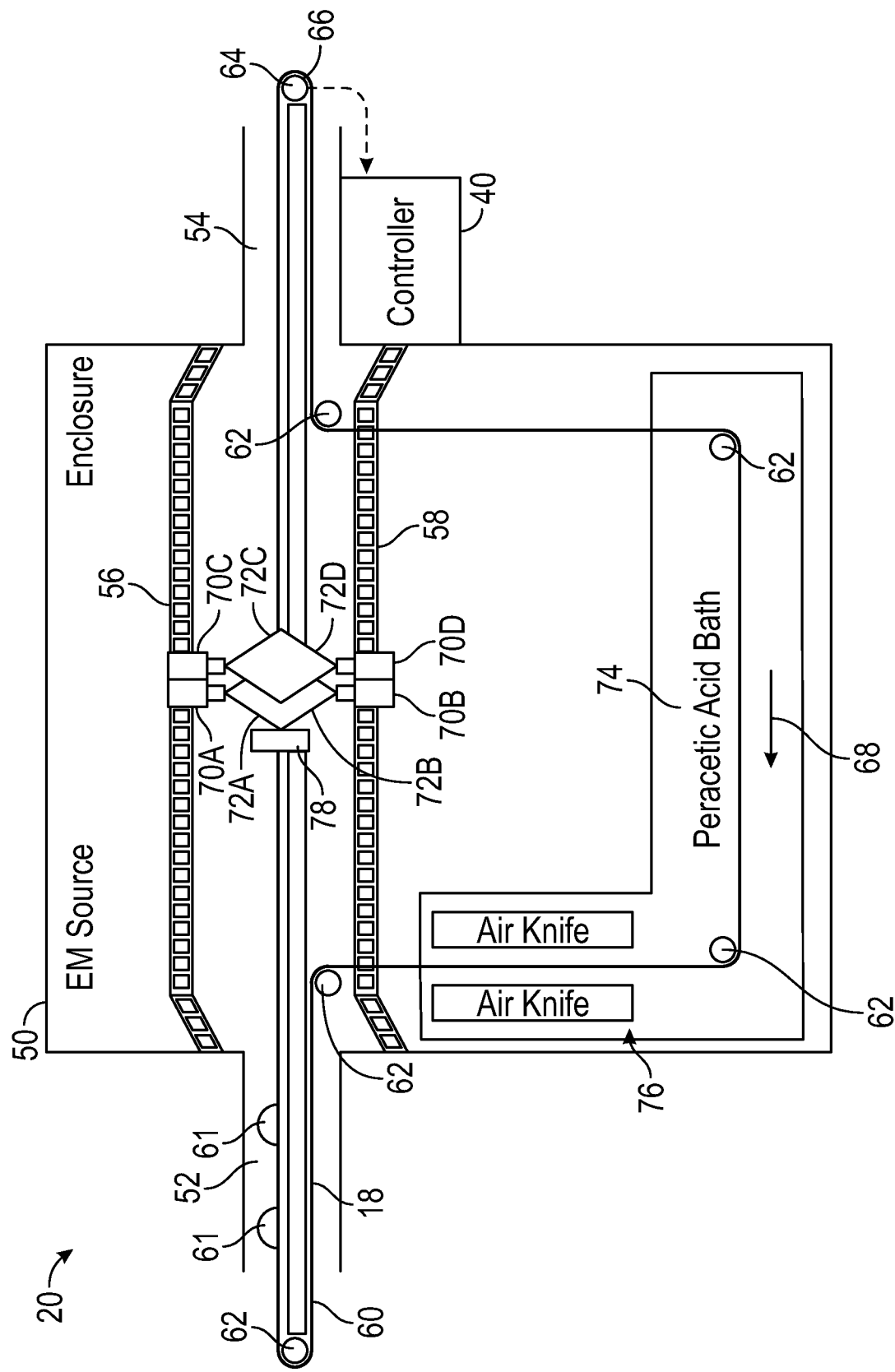
FIG. 2 is a detailed diagrammatic view of the imaging system of FIG. 1.

Referring now to FIG. 2, the imaging system 20 and the transparent conveyor belt system 18 of the inspection system are illustrated in further detail. The imaging system 20 includes an enclosure 50 that has an inlet opening 52 that is used for receiving pieces on the transparent conveyor belt system 18. The enclosure 50 also has an exit opening 54 for the transparent conveyor belt system 18 leaving the enclosure 50. The enclosure 50 provides an environment so that external electromagnetic radiation does not interfere with the imaging system 20. The enclosure 50, in some examples, may not be required. The enclosure 50 may be formed of various materials and have access openings to allow access to components therein.

The enclosure 50 has a first EM source 56 and a second EM source 58 disposed therein. The first EM source 56 is disposed above the transparent belt and directs electromagnetic radiation on the part to be inspected. The second EM source 58 is disposed below the transparent conveyor belt system 18 and directs the light therethrough toward the piece to be imaged. Various types of electromagnetic radiation may be generated from the EM sources 56, 58 such as but not limited to visible light (from a visible light lighting system), infrared light (both near and far), ultraviolet light, radio waves and X-rays. The wavelength of EM radiation may vary depending on the types of pieces and the types of defects being detected. As illustrated, the EM sources 56, 58 are composed of a plurality of elements. The elements may generate the same band of wavelengths or may generate various bands of wavelengths (equivalently frequencies) that, in combination, are used to illuminate the part to be inspected. For example, separate images at different wavelengths may be used to determine the presence of one or more defects. The use of several light or EM sources used to obtain several images at different frequencies may be referred to as "multispectral", in the case of more than one, but less than 10 bands of electromagnetic (EM) wavelengths are used, or "hyperspectral" if 10 or more bands of EM wavelengths EM frequency bands generated.

The transparent conveyor belt system 18 has a transparent belt 60 through which the electromagnetic (EM) radiation from the second EM source is transmitted to illuminate a piece 61 being inspected. The transparent belt 60 receives the piece 61 from the placement system 12 as mentioned above. The transparent belt 60 is routed using a plurality of rollers 62 and a motor 64. The motor 64 may have an encoder 66 thereon. The encoder 66 allows feedback as to the position of the transparent belt 60. The position of the transparent belt 60 may be used for identifying the piece 61 being conveyed through the imaging system 20. That is, when the piece 61 reaches the field of view the position of the encoder is used to identify the piece for remediation and tracking purposes.

The transparent belt 60 moves in the direction illustrated by the arrows 68. The movement of the transparent belt 60 positions the pieces 61 to be inspected relative to imaging devices 70A, 70B, 70C and 70D, each of which has a unique identifier. In the present example, four imaging devices 70 are provided. However, fewer than four or more than four may be used depending on the complexity and size of the piece to be inspected. The imaging devices 70A-70D are collectively referred to as the imaging device 70. Each imaging device 70 may be formed of a camera that has a sensor therein. The imaging device 70 may be a charged coupled device, a CMOS device or other electro-optical type of sensor used to generate an image signal. The imaging devices 70 receive the wavelengths desired in later analysis. Some imaging devices may receive many wavelengths, referred to as "multispectral imaging" in the case of less than 10 EMF bands, or "hyperspectral imaging", in the case of more than 10 EMF bands. The information from some of the EMF bands might not be useful in the analysis. To increase analysis efficiency, only the EMF bands that have been predetermined to be useful for identifying the defect type may be selected for use in the analysis. In this manner, the information from the EMF bands is used to perform the analysis, referred to as "multispectral analysis" in the example of using 10 or less bands, or "hyperspectral analysis" in the example of more than 10 EMF bands. Further, multiple imaging devices 70 may be used when an imaging device cannot receive all the desired wavelengths. The image signal or signals may have data associated with such as the identifier of the imaging device, a gain setting, a wavelength identifier, and the encoder position of the belt. The imaging devices 70 each have a field of view 72A-72D, respectively. In the present example, the field of views 72A and 72B are aligned and capture images of opposite sides of the piece. Likewise, the fields of view 72C and 72D are aligned and capture images of opposite sides of the piece. The imaging devices 70A and 70C are spaced apart and thus the fields of view 70A and 70C are spaced apart. Likewise, the imaging devices 70B and 70D are spaced apart and therefore their fields of view 72B and 72D are spaced apart.

The number of fields of view correspond to the number of cameras. In one example, for determining defects of a chicken piece, it was found that providing two different images of the same piece with different gain settings of the imaging devices 70 enabled different defects or different defect locations to be determined. For example, high gain allowed filaments around the perimeter of the part to be determined. Low gain is used to determine filaments in the surface of the chicken piece. In one example, the gains above the transparent belt (A first and third gain were different and a second and fourth gain of the image devices below the transparent belt were different—one high, one low). In another example the first and second image device gains were the same, the gains of the second and fourth image device were the same and the gains of the first and second image devices was different the gains of the third and fourth image devices. That is, one pair was high, and one pair was low.

The fields of view 72B and 72D extend through the transparent belt 60 to obtain images of the underside of the piece. Therefore, a clean transparent belt 60 allows the most accurate images to be captured. In this example, a bath 74 is used for cleaning the transparent belt 60. The bath 74, in this example, is an acid bath formed using peracetic acid. The transparent belt 60 is routed within the enclosure 50 into the bath 74. As the transparent belt 60 is routed toward the inlet opening 52, a belt cleaning system 76 such an air knife system is used to remove the liquid from the transparent belt 60. The belt cleaning system 76 may also include the acid bath 74. Therefore, the image from the imaging devices 70B and 70D are free from false detections. A photo trigger 78 triggers the imaging devices 70A-70D to generate an image when a piece disposed on the transparent belt 60 enters the respective fields of view 72.

As mentioned above, the imaging devices 70 form an image of the piece being inspected with each of the field of views. Also, as mentioned above, the EM sources 56, 58 may be one of a variety of types of EM sources. Also, as mentioned above, various types of electromagnetic radiation may be generated from the EM sources 56, 58. The electronic images and the electronic imaging signal generated by the imaging devices 70A-70D may correspond to the image based upon the type of electromagnetic radiation. For example, visible light, infrared, ultraviolet and x-rays are examples of suitable electromagnetic radiation. Various image signals of a piece may be taken using different types of electromagnetic radiation to detect different types of defects. The EM sources 58 may be flashed for image capture or illuminated constantly.

Figure 3A:
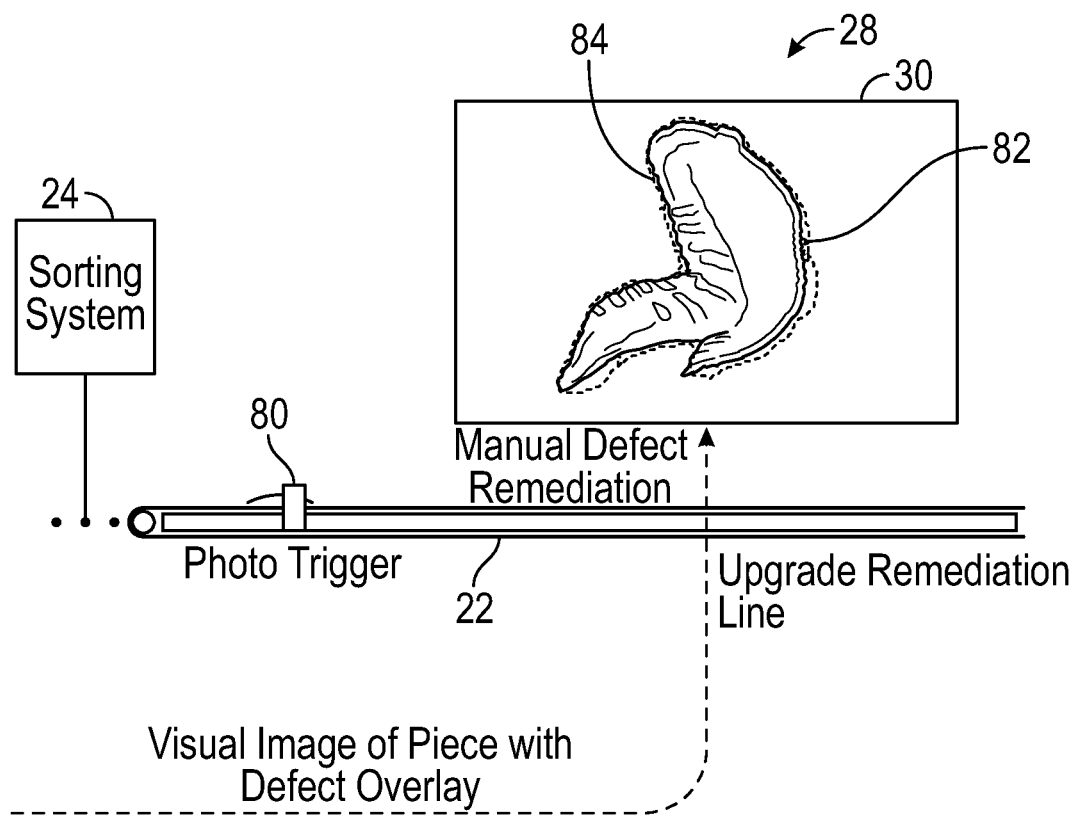
FIG. 3A is a diagrammatic view of a manual remediation system.

Referring now to FIG. 3A, the sorting system 24 and one example of a manual remediation system 28A is set forth. In this example, the sorting system 24 sorts the pieces based upon the images obtained from the imaging devices 70. A photo trigger 80 may trigger the display 30 to display an image of the piece. The piece may have indicia such as a location 82 highlighted for remediation of the piece. Once the piece travels to the remediation site, the photo trigger 80 triggers the image of the piece with the location 82 of the defect highlighted as an overlay on the image. A mask 84 that is described later is illustrated. The mask 84 represents the area outside of which is not considered in the defect determination. The mask 84 may not be displayed. Once the remediation is performed, the piece may be placed on the conveyor belt system 22 to be reinspected or placed in a predetermined grade bin or container for shipment.

Figure 3B:
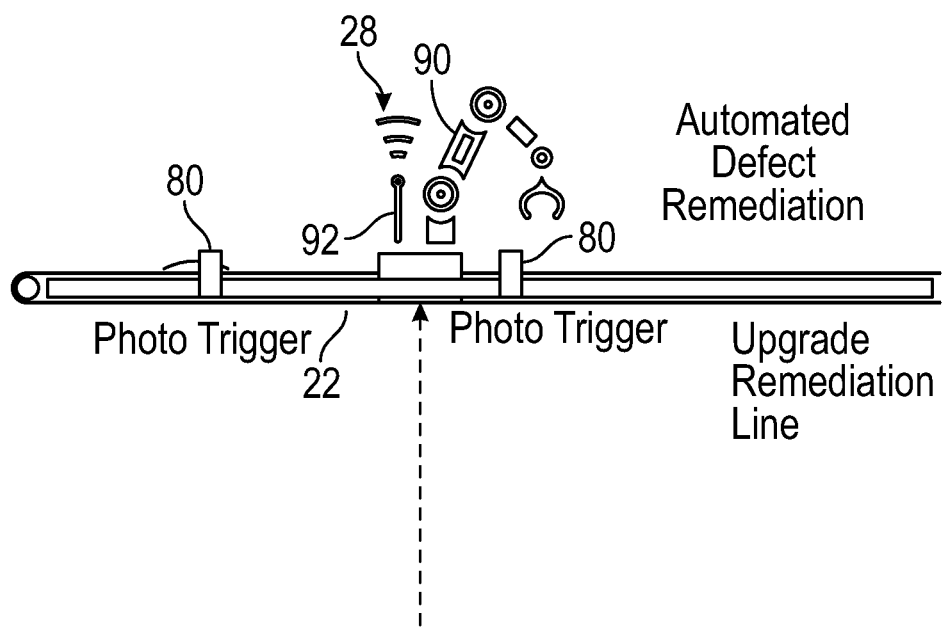
FIG. 3B is a diagrammatic view of an automated remediation system.

Referring now to FIG. 3B, an automated remediation system 28B for mechanically removing a defect is set forth.

In this example, a robot 90 receives coordinates of a detect and an identifier for the piece. The robot 90 may manipulate the piece such as cutting or plucking and replace the piece on the conveyor 22. The piece data may be communicated through an antenna 92 wirelessly to the robot 90. Of course, other types of communication may take place such as a wired connection. Because of the location of the defect and the type of defect is known, the robot 90 may perform the appropriate remediation. Different types of machines may be used for different types of remediation of different types of defects. Thus, the sorting system 24 routes the piece to the appropriate manual remediation system 28A or automated remediation system 28B. Other types of systems may perform different types of remediation. That is, some may use a combination of hand remediation and automated or machine remediation or two different types of automated remediation. Because the coordinates of the defect, the size of the defect, the type of the defect and the type of piece on which the defect occurs is known, the defect may be quickly remediated. Other types of defects or a high severity of a defect may cause the piece to be rejected all together.

Figure 4:
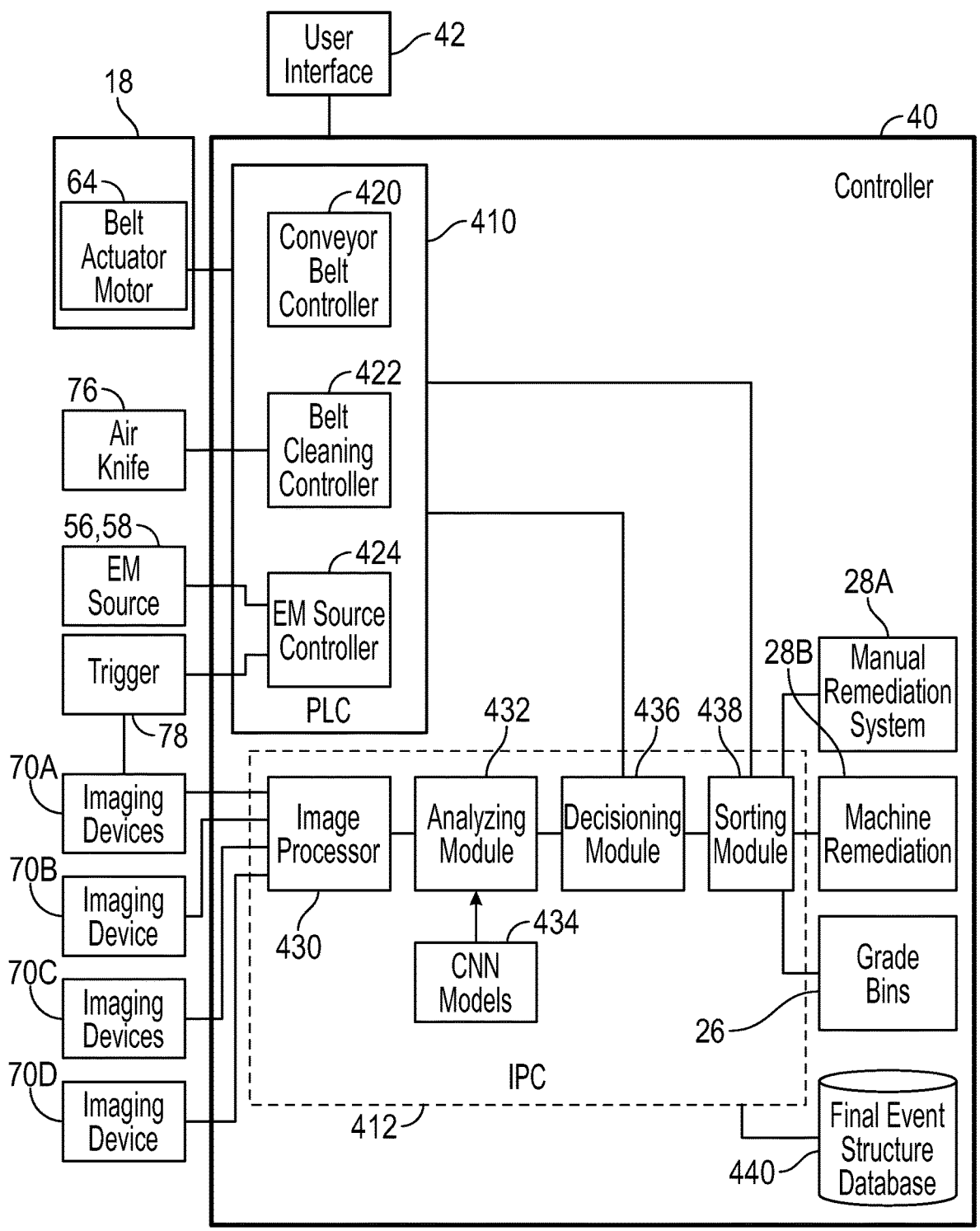
FIG. 4 is a high level block diagrammatic view of an example of the controller.

Referring now to FIG. 4, the controller 40 is illustrated in further detail. In this example, the controller 40 is divided into two general functions including a programmable logic controller (PLC) 410 and an industrial personal computer (IPC) 412. While the names programmable logic controller and industrial personal computer are set forth, different types of controllers, different numbers of controllers and locations of controllers may be changed depending upon various system requirements. The programmable logic controller 410 includes a conveyor belt controller 420, a belt cleaning controller 422 and an EM source controller 424. The conveyor belt controller 420 may control the speed and position of the belt actuator motor 64 and therefore the transparent conveyor belt 60. The belt cleaning controller 422 may activate the air knife when the belt is moving. The EM source controller 424 controls the EM sources 56, 58 based upon the trigger 78. In summary, the PLC module controls the movement and timing of the conveyor belt, the cleaning system and the electromagnetic source controller.

The IPC 412 receives signals from the image devices 70A-70D and communicate them to an image processor 430. The image processor receives signals from the image devices that correspond to the top and bottom signals of a piece that is being inspected. As mentioned above, the image devices may have different gains set for the different positions. This may allow different types of defects to be observed. An analyzing module 432 uses a convolutional neural network (CNN) model that allows for continuous improvement of the identification of defects and of the piece types.

Figure 5:
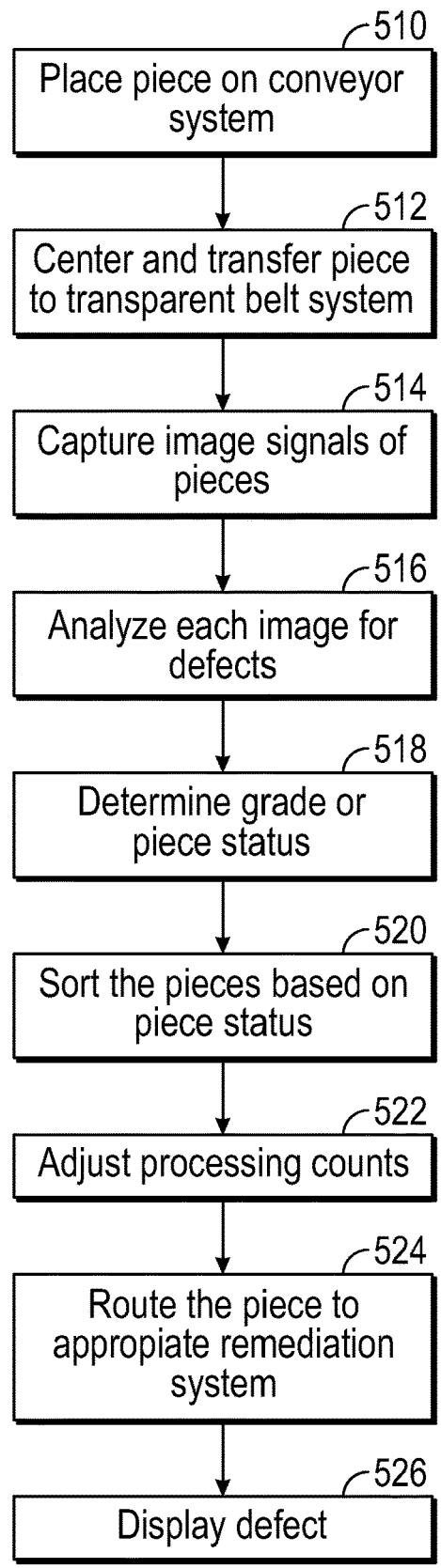
FIG. 5 is a high level flowchart of a method for operating the inspection system.

Referring now also to FIG. 5, a high-level method for inspecting and processing is set forth. In step 510 a poultry piece is placed on the conveyor belt system 14 by the placement system 12 with a specified space gap or space from other pieces. This step may be optional if direct placement onto the transparent belt system 18 is performed.

In step 512, the poultry piece is centered and transferred to the transparent belt system 18 prior to entering the image capture enclosure 50.

In step 514, once in the image capture enclosure 50, image signals of top and bottom views of the poultry piece are captured with the imaging devices and the EM sources 56, 58. An image signal for each field of view is obtained.

In step 516, the images are transmitted to the IPC 412 and the analyzing module 432 analyzes each image. The analyzing module 432, uses image filters and the convolutional neural network (CNN) models 434, and extracts information from each image related to the piece (poultry-piece features) as well as detailed information of each defect found (defect-candidate features) on the piece. The type of defect, the area of the defect, the location of the defect, the sum of defects and the like may be determined.

Ultimately, in step 518 the extracted data from the image are passed to the decisioning module 436 where additional computations are performed and piece batch level customizable thresholds are applied to determine a piece status. The piece status may include but is not limited to determining piece status such as a piece grade (0, 1, 2 . . . n) or identify the piece as invalid (wrong piece type) or indicate the piece as reevaluate (needs to go through image capture again).

In step 520 the piece status (grade/invalid/reevaluate pieces) is communicated to the programmable logic controller 410 to direct the appropriate conveyor belt controller 420 to control the dropout sort to occur based on the grade bin specified (targeted sort dropout) and the target encoder position (piece position on the belt).

In step 522 the piece processing counts (total, by grade, invalid, reevaluate) will be appropriately adjusted based on the piece status and the count updated in the database 440 in the decisioning module 436.

In step 524, the graded pieces requiring remediation are route the pieces to the appropriate conveyor line to the appropriate remediation system 28. A visual or automated remediation process is invoked once the pieces are positioned in front of either remediator for manual processing or a mechanical device for automated processing. To aid in manual processing, the piece image will be presented to the remediator with defects marked in step 526.

The analyzing module 432 described above leverages various convolutional neural network (CNN) models 434. A brief description is provided on the lifecycle of continual improvement of the CNN models 434. The CNN models 434 are built by using representative images (training sets) of poultry pieces with the targeted visual defects. For the image classification models those images are labeled with defect types visually seen in the image. For object localization/detection models, the defects are highlighted (annotated) on the images so that the CNN model 434 can learn to identify the location and size of the defect. Once the training set is labeled/annotated the CNN models are built. Each model is installed into the analyzing module 432 and is communicated to the production line industrial personal computer (IPC) 142. The IPC 142 is signaled at the agreed upon scheduled time to bring the Analytic Pipeline online for use.

In one example, for a defined period, poultry piece images will be saved with all the poultry-piece and defect-candidate features extracted from the analyzing module 432 and decision module 436.

A maintenance process may be run on a regular basis to generate a distribution report of key processed piece features with marginal or low confidence scores as well as a list for manual inspection. The piece images identified in the manual inspection list may be visually inspected and actions taken to improve the confidence score if deemed appropriate. Actions could involve labeling the image (image classification model) or annotating the defects (object localization/detection model) then adding them to the appropriate training set for a future model version build.

In general, the image processor 430 establishes a connection to each camera, loads the appropriate profile, and brings each camera online for image acquisition. On receipt of an image signals from the imaging devices 70, the analyzing module 432 which includes image processing, deep learning image classification, and object localization/detection tasks for applying the image filters, extracts both poultry-piece features and defect-candidate features from the piece image. For each image capture from the field of views 72, the analytics process is performed. Once all the image signals have been processed by the analyzing module 432, the decision module 436 determines the presence of defects. The method processes both the poultry piece features, and defect candidate features collected, resulting in a piece grade determination which is communicated a final event structure database 440. Ultimately, the sorting module 438 may sort the pieces based on the defects. The controller 40 is coupled to the final event structure database 440 that is used to store various data and other numerical identifiers including but not limited to a bin number, the encoder position of the piece that is used as a piece identifier, images from each imagining device, area measurement, coordinates of the defects, perimeter coordinates of the piece, a center X/Y reference point, counts and the like.

For pieces presented for further remediation, invocation of visual and mechanical aids in the remediation process by displaying defect areas on a display 30 for manual remediation. For machine remediation, each defect candidate area location information of the piece at the time of image capture, is available for use by a machine interface.

Figure 6:
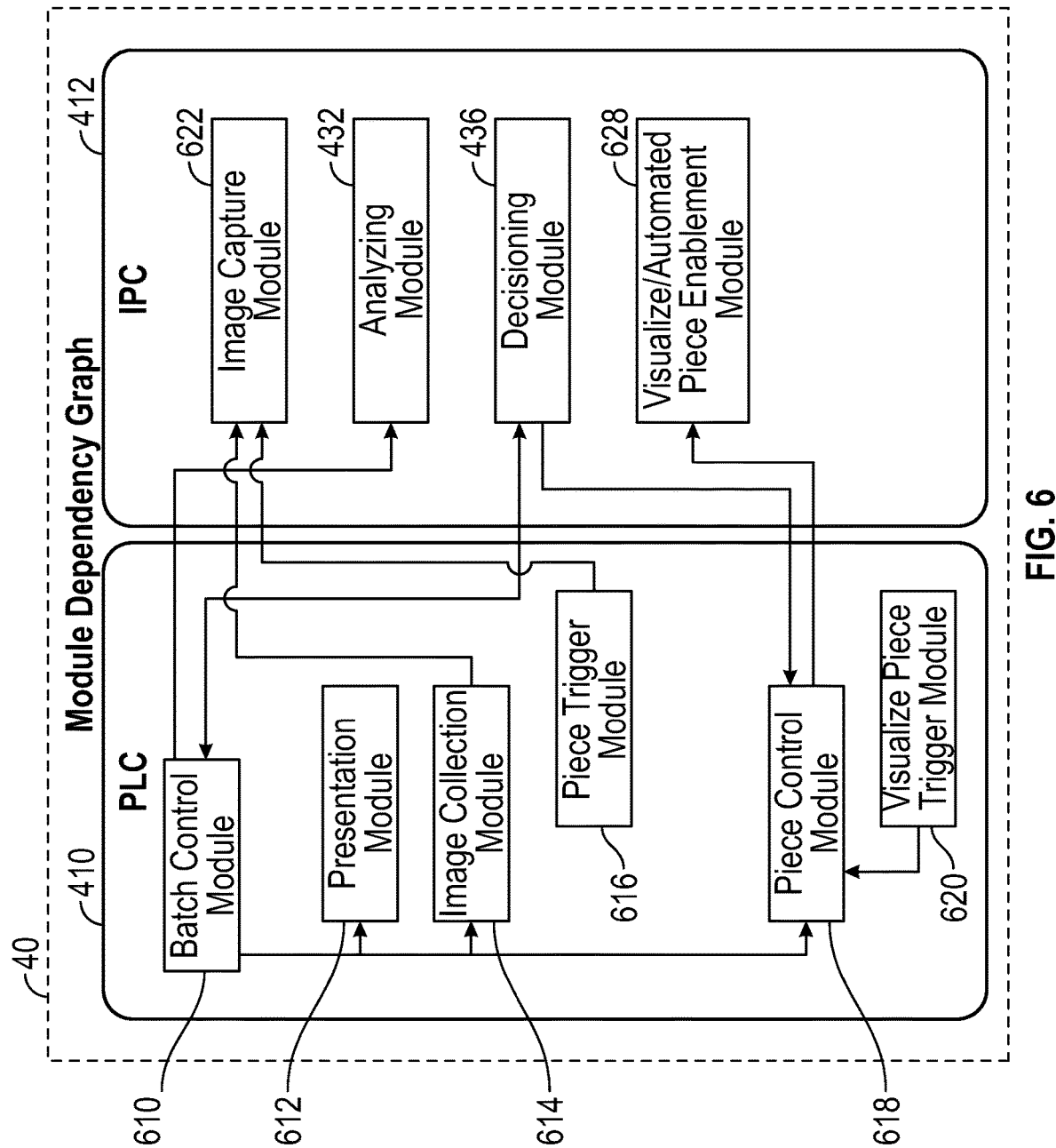
FIG. 6 is a detailed diagrammatic representation of the control modules of the PLC and the IPC.

Referring now to FIG. 6, a more detailed layout of the software control modules in the PLC 410 and the IPC 412 of the controller 40 and their interactions are set forth at a high level. In the PLC 410, a batch control module 610 is set forth. The batch control module 610 is a component that provides generates a screen display for the user interface 42 for setup of a batch for processing. The batch control module 610 enables manual starting/resuming and stopping/pausing of the processing system, and reports on batch processing statistics when complete.

The PLC 410 also includes a presentation module 612. The presentation module 612 manipulates a group of chicken pieces and places them onto the middle of a moving conveyor belt, with a predetermined separation between the pieces.

An image collection module 614 in the PLC 410 communicates the batch number and piece type to an image capture module 622. The batch started/stopped status for camera online/offline processing may also be provided. The image collection module 614 also enables/disables power to the physical cameras and lighting or EM sources.

A piece trigger module 616 of the PLC 410 generates a trigger signal from the trigger 78 when the piece is in the field of view (FOV) 72 and ready for capturing of the image.

A piece control module 618 controls the transparent conveyor belt system 18 to carry the piece through the light controlled enclosure 50 for image capture and controls the disposition of the piece once the decisioning module 432 has determined the piece grade bin. Integrated into the piece control module 618 is a belt cleaning control system that controls the belt cleaning system 76 such as the air knife that cleans the belt on a continuous basis.

The visualize piece trigger module 620 generates a signal that is communicated to the piece control module 618 when a piece requiring remediation has been routed to the appropriate remediation system 28 and will present the image of the piece with all defect areas visualized on the display 630.

The IPC 412 has the image capture module 622 described above. The image capture module 622 manages the imaging devices 70 for the capture of an image signal corresponding to an image of the piece. The image signal is communicated to an analyzing module 432 for defect analysis. The analyzing module 432 and provides the information to the decisioning module 436.

The decisioning module 436 implements the decision module 436 and notifies the piece control module 618 to direct the piece to the grade bin assigned.

A visualize/mechanical remediation enablement module 628 implements the visualization and remediation method described in further detail below.

In the following details of the operation of the modules are set forth.

Figure 7:
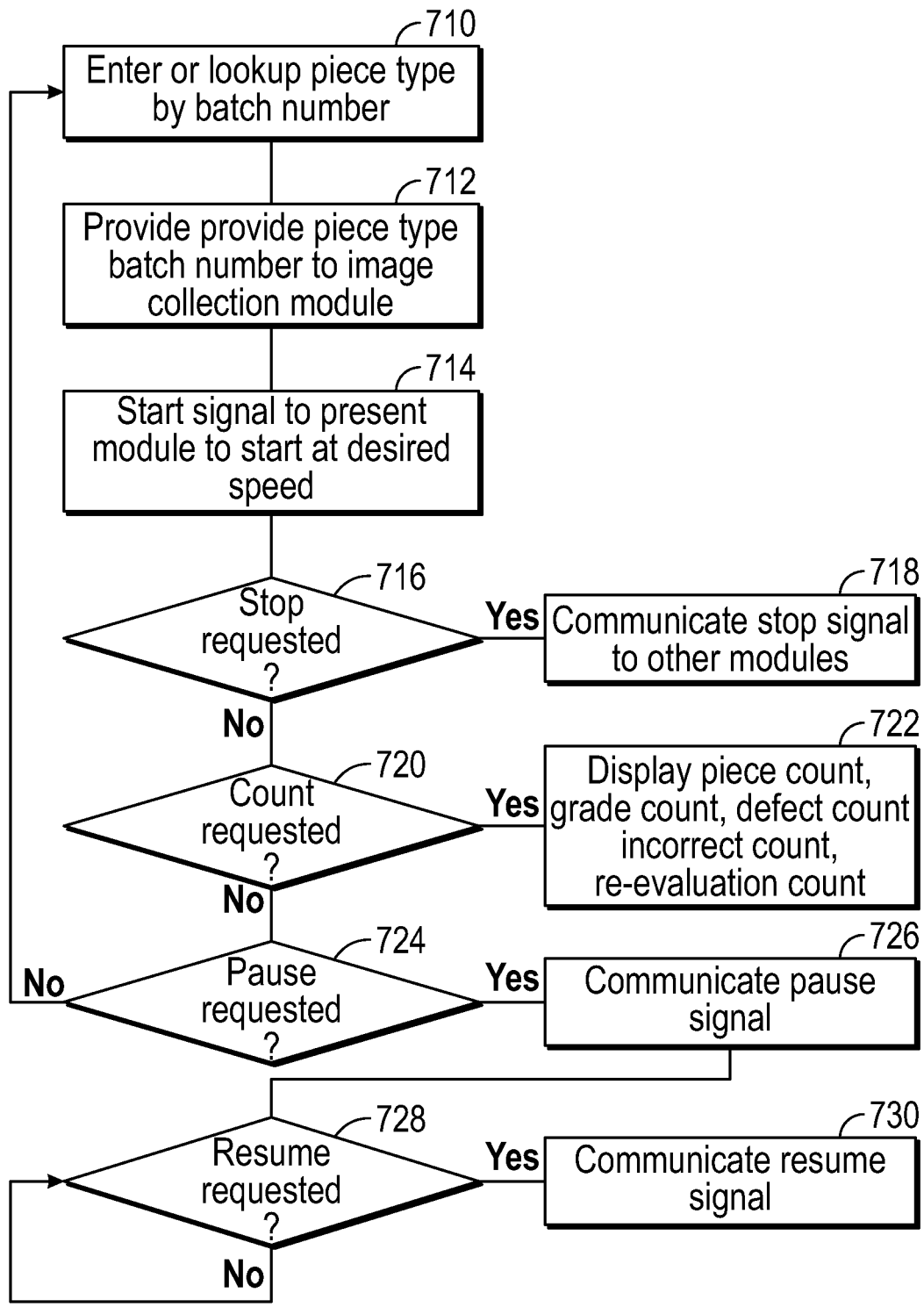
FIG. 7 is a flowchart of a method for operating the batch module.

Referring now to FIG. 7, a flowchart for operating the batch control module 610 is set forth. In this example, the piece type is looked up or entered by identifying the batch number in step 710. The user interface 42 may be used to enter the piece type through prompts displayed on the display 44. In step 712, the piece type and the batch number are provided to the image collection module 614. The system is then ready to start processing.

A start signal is communicated to the presentation module 612 from the batch control module 610. A desired speed may be entered or previously provided by the batch number. In step 714, the start signal is communicated to the start module to start processing at the desired speed. In step 716, when a stop signal is requested by the operator by hitting a stop button or communicating a stop signal through the user interface 42, a stop signal is communicated to the other modules in step 718. In step 716, when the stop signal is not requested, step 720 is performed. In step 720, when a count is requested through interaction with the user interface 42, step 722 displays a count such as a piece count, a grade count, a defect count, an incorrect piece count or re-evaluation count. The piece count may correspond to the total pieces processed. The grade count may provide a count of the number of pieces from a batch within each of the grades. A defect count corresponding to the number of pieces for each defect may be provided. An incorrect piece count or a re-evaluation count may also be provided for the number of pieces that were incorrect in a batch or pieces that needed remediation within a batch.

In step 720, when a count is not requested, step 724 determines whether a pause has been requested. When a pause has been requested, a pause signal is communicated to the presentation in step 726. Pausing may be used to adjust the process or equipment.

In step 724, when a pause has not been requested, the process repeats again in step 710. After step 726, when a pause signal is communicated to the presentation module 612 and the piece control module 618, step 728 is performed. Step 728 is determined whether a resume signal has been requested. When a resume signal has been requested, the resume signal is communicated to the presentation module 612 and the piece control module 618 in step 730. When a resume has not been requested, step 728 is repeated.

Figure 8:
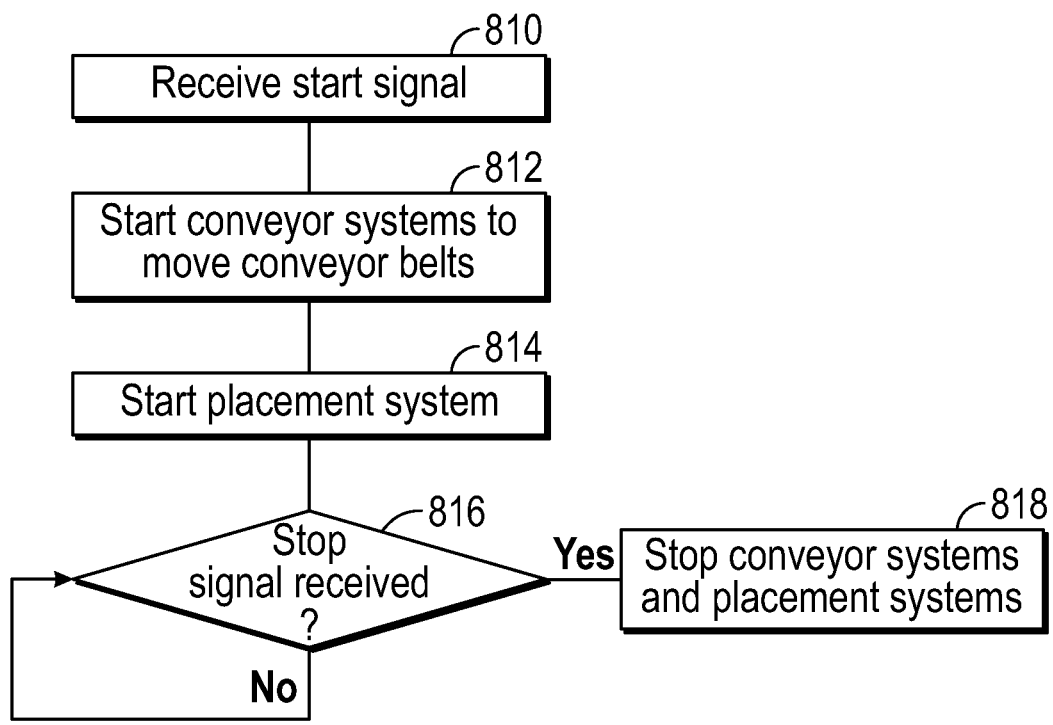
FIG. 8 is a flowchart of a method for operating the presentation module.

Referring now to FIG. 8, the operation of the presentation module 612 is provided in more detail. The presentation module 612 controls the positioning of chicken pieces in the middle of the moving conveyor belt with a predetermined spacing therebetween. In step 810, a start signal is received. In step 812, the conveyor systems are provided with a signal to control the movement of the conveyor belts. In step 814, the placement system 12 of FIG. 1 may be operated to allow the singulator or other placement system to position the pieces on the conveyor belt at a predetermined speed and at a predetermined spacing. After step 814, step 816 determines whether a stop signal has been received. When a stop signal has been received, step 818 stops the conveyor system and the placement system.

Figure 9:
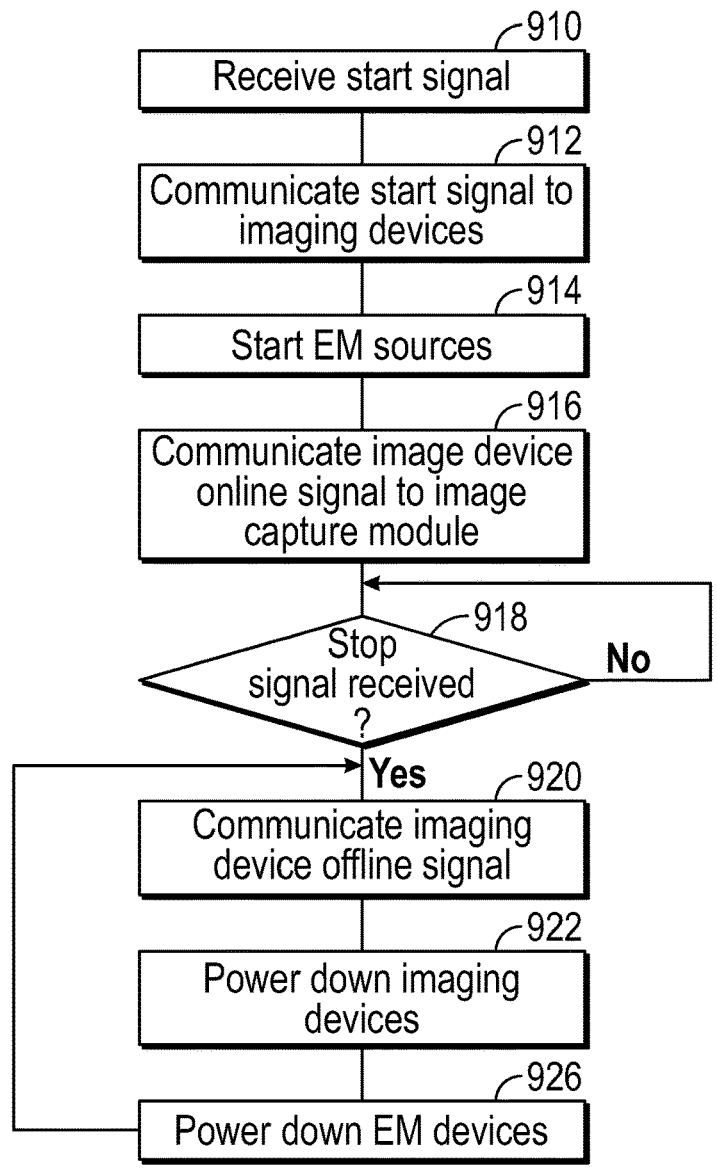
FIG. 9 is a flowchart for operating the image collection module.

Referring now to FIG. 9, the operation of the image collection module 614 is described in further detail. In general, the image collection module 614 communicates the batch number in pieces to the image capture module 622 as well as determining whether the batch has started and stopped for the imaging devices. In step 910, a start signal is received. The start signal may have data such as a start flag, the batch number, the piece type and the processing speed. The start signal is communicated to the imaging devices in step 912. In step 914, the electromagnetic radiation sources are started. In step 916, an image device online signal is communicated to the image capture module 622. After step 916, it is determined whether a stop signal has been received in step 918. When a stop signal has not been received, step 918 is again performed. After step 918, when a stop signal has been received, an imaging device offline signal is generated in step 920. In step 922, the imaging devices are powered down in response to the imaging device offline signal. In step 926, the electromagnetic radiation generating devices are powered down.

Figure 10:
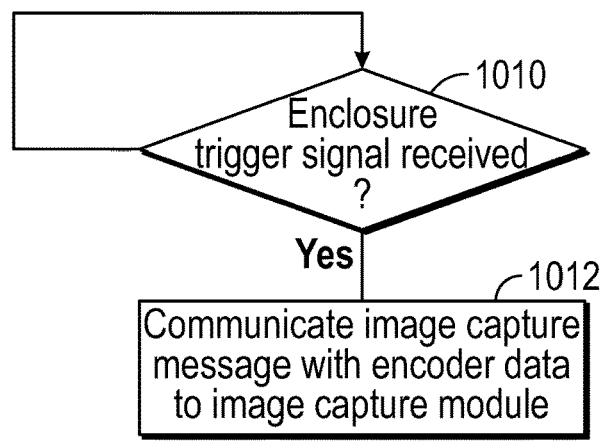
FIG. 10 is a flowchart for operating the trigger module.

Referring now to FIG. 10, the operation of the piece trigger module is set forth. The piece trigger module 616 is module that is activated in response to the trigger within the enclosure 50. In step 1010, when an enclosure trigger signal is received, step 1012 communicates an image capture message with the encoder data of the transparent conveyor belt system 18 to the image capture module 622. In step 1010, when an enclosure trigger signal is not received, step 1010 repeats to await the next piece.

Figure 11:
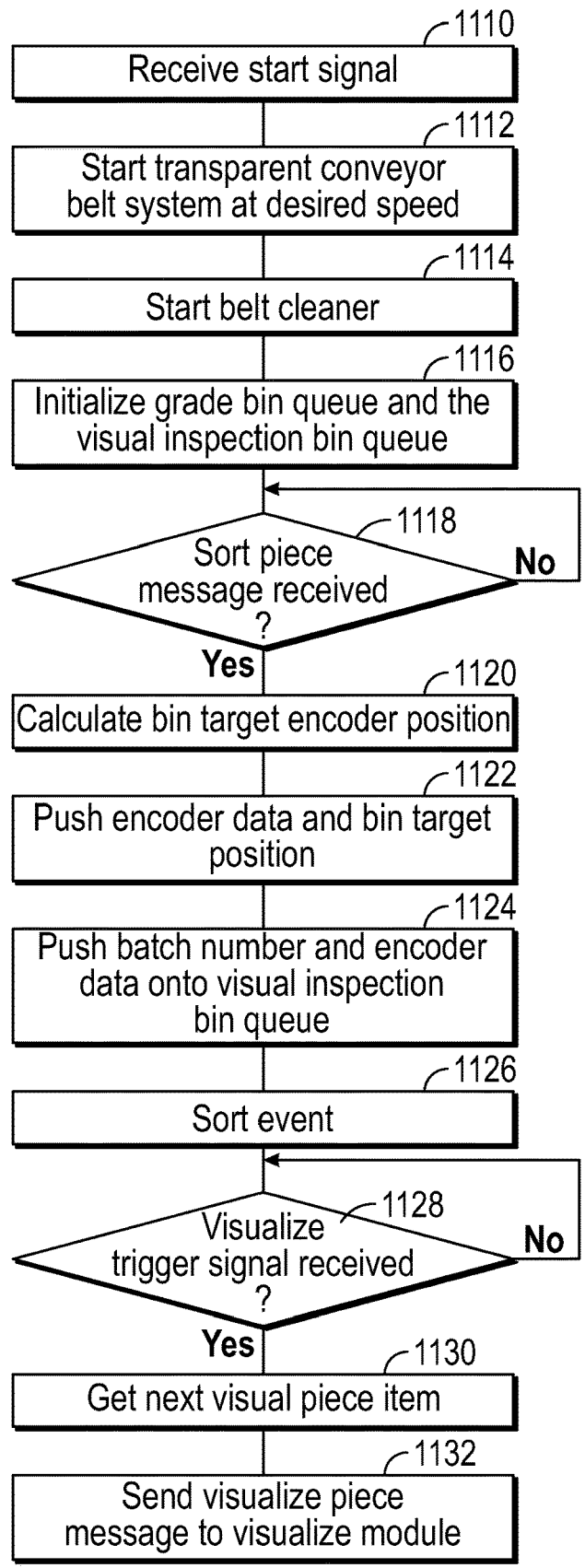
FIG. 11 is a flowchart for operating the piece control module.

Referring now to FIG. 11, the operation of the piece control module 618 is described. The piece control module 618 operates the transparent conveyor belt system 18 that is used to carry the pieces through the enclosure 50 for image capture and ultimately the disposition of the piece once the decisioning module 436 determines the piece to be defect free, defective or an incorrect piece. The belt cleaning system 76 such as the air knife is operated in response to the piece control module 618. In step 1110, a start signal is received. In response to the start signal, the transparent conveyor belt system is started at the desired speed in step 1112. In step 1114, the belt cleaning system 76 is started. In step 1116, the grade bin queue, and the visual inspection bin queues are initialized. In step 1118, it is determined whether a sort piece message has been received. The sort piece message may include a batch number, encoder data and the grade bin number. When a sort piece message has not been received, step 1118 is again repeated. In step 1118, when a sort piece message has been received, step 1120 calculates the bin target encoder position. The bin target encoder position is calculated using the messaging encoder data and the distance constant associated with the specified grade bin number. Step 1122 pushes the encoder data and bin target position into the queue. In step 1124, the batch number and encoder data is pushed onto the visual inspection bin queue. In step 1126, a method may be performed in which the sorting system is operated to route the piece to its desired position. Sorting maybe performed by placing various grade pieces into bins or containers, rejecting failed pieces or pieces of the wrong type. In step 1128, when a visualized trigger signal is not received, step 1128 is again performed. In step 1128, when a visualized trigger signal is received, the next piece to be visualized is obtained from the queue. A visualized piece message is communicated to the visualize/ automated piece module 628. The batch number and the piece number are all communicated in the visualized piece message.

Figure 12:
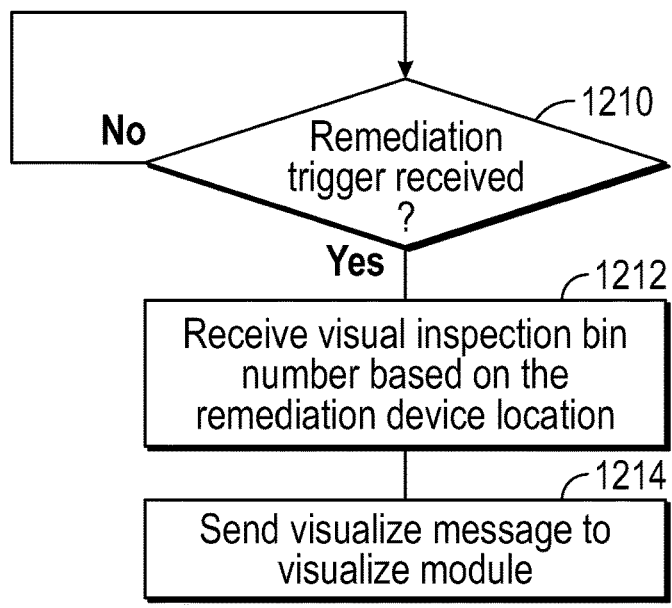
FIG. 12 is a flowchart of operating the remediation trigger module.

Referring now to FIG. 12, the visualized piece trigger module 620 is described in further detail. The visualized piece trigger module 620 signals the piece control module 618 when a piece require remediation has been routed to a remediation system. In step 1210, when a remediation trigger signal has not been received, step 1210 repeats. In step 1210, when a remediation signal has been received, step 1212 receives a visual inspection bin number for the remediation device location to obtain the data for the next defective piece. In step 1214, a visualize message is communicated to the visualize/automated piece enablement module 628. This allows the visualize module 628 to present an image of the piece to be processed as well as the defect location, type of defect and the like.

Figure 13:
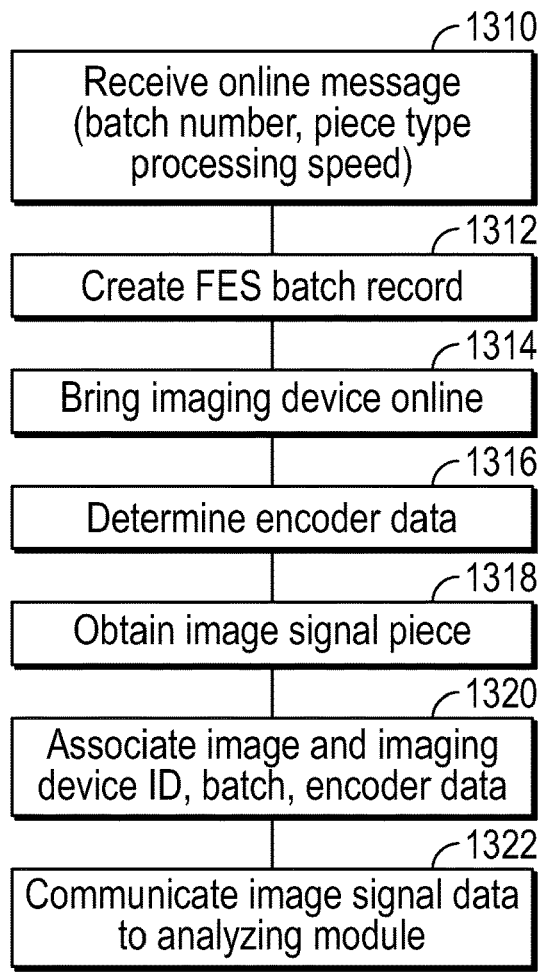
FIG. 13 is a flowchart of a method for operating the image capture module.

Referring now to FIG. 13, the image capture module 622 is described in further detail. In step 1310, an online message is received. A batch number, piece type and processing speed may all be communicated in the online message. In step 1312, a final evaluation structure (FES) batch record may be provided that includes the batch number, piece type, processing speed and a time stamp for starting the process. In step 1314, the imaging device is brought online. Each of the imaging devices may be brought online in response to the online message from step 1310. In step 1316, the encoder data is captured from the encoder 66 that moves with the transparent conveyor belt 60. The encoder signal from the encoder 66 may be obtained by the PLC so that the data is coordinated. The PLC may communicate the data to other modules. In step 1318, an image signal is obtained for the piece. An image signal may be generated at each of the imaging devices. In step 1320, the image signal and the imaging device identifier, the batch and the encoder data are all associated. In step 1322, the image is ultimately communicated to the analyzing module 432. The image along with the image signal data, such as the piece image reference, a camera identifier, a batch number and the encoder data, may all be communicated.

Figure 14A:
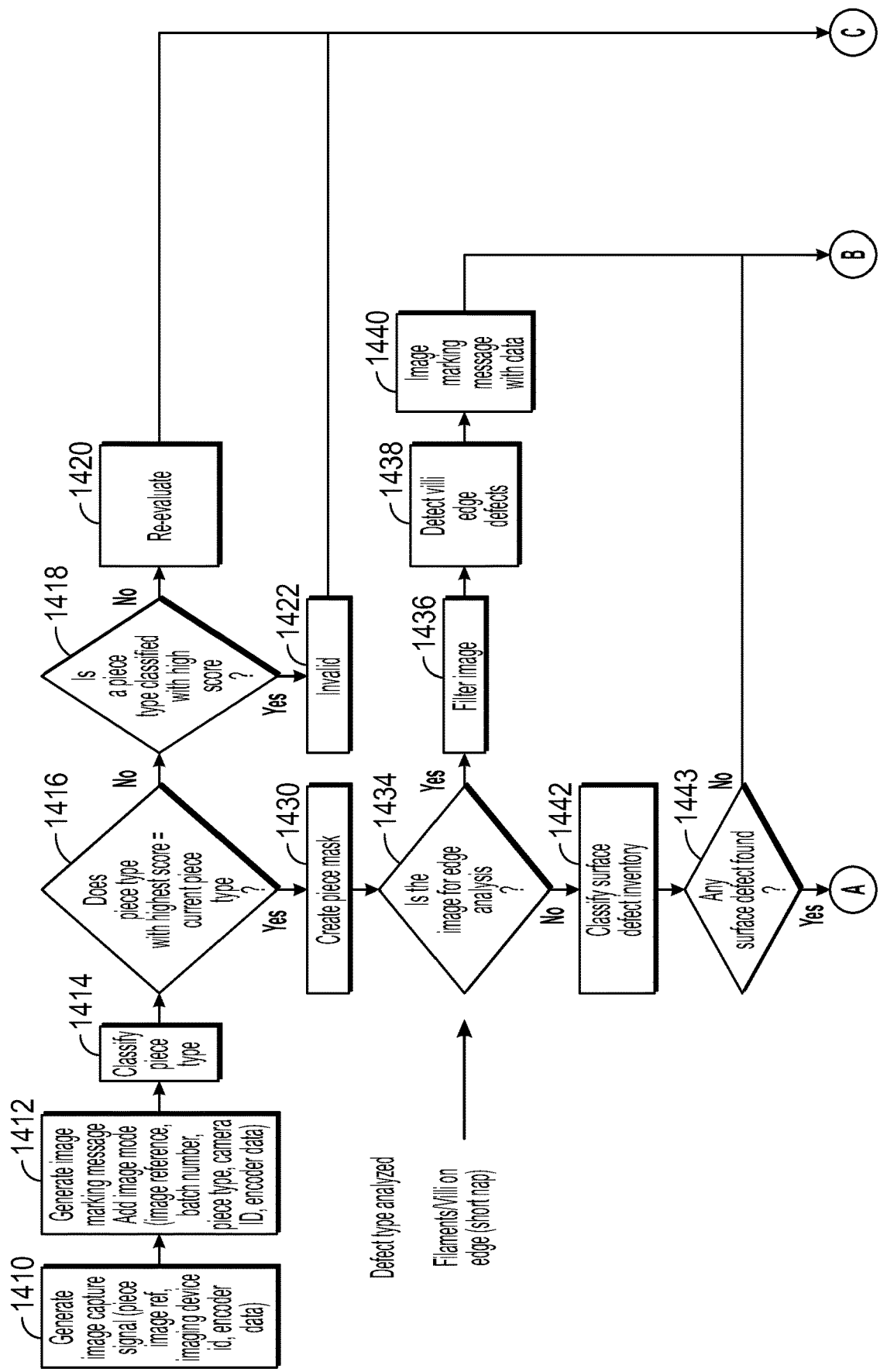
FIGS. 14A-14C is a flowchart of a method for operating the analysis module.
Figure 14B:
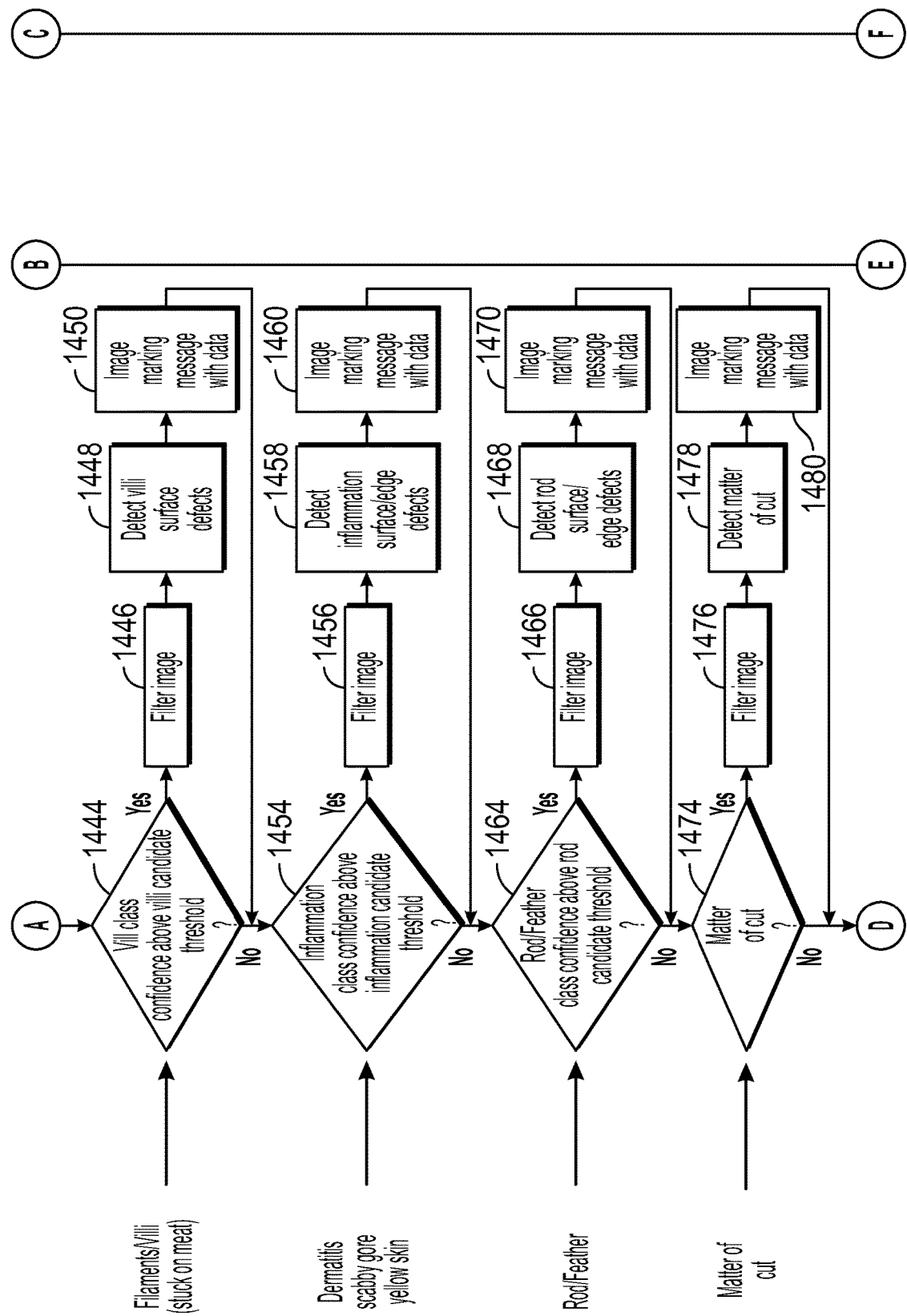
Figure 14C:
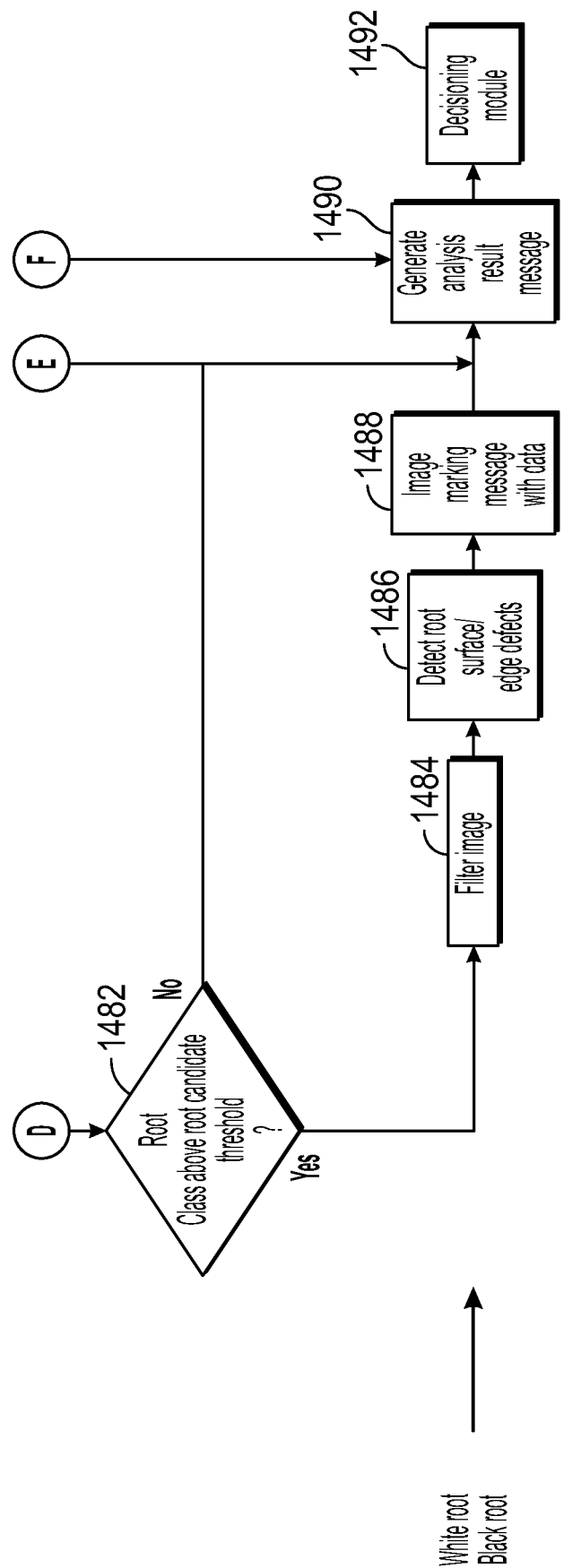

Referring now to FIGS. 14A, 14B and 14C, the operation of the analyzing module 432 is provided in further detail. The analyzing module 432 uses multiple deep-learning image classifier modules to determine if a piece is defective or requires upgrade remediation, to identify and grade the defects and provide the information to the decisioning module 436. In step 1410, the image capture signal is received from the image capture module 622. As mentioned above, the image capture signal may include a piece image reference, an imaging device identifier and encoder data. The piece image reference may provide an image for each of the imaging devices. In step 1412, an image marking message may have an image node marked thereon. The image node may be formed that includes the image reference, the batch number, the piece type, the camera identifier and the encoder data. As mentioned above, the encoder data is used to identify the piece by the position.

In step 1414, the piece is classified as to piece type which may have a corresponding numerical identifier. Various piece types may be classified such as wings, thighs, drumsticks, breasts and the like. The piece type classifier that classifies the piece type may generate a numerical identifier score for each of the various types. Step 1414 may use a deep learning image classification model that is invoked to extract the poultry-piece: piece-type feature by chicken piece deep learning image classification. The processing batch is typically one-piece type.

If the piece type matches the batch specified piece type, a poultry-piece: decision-status feature is set to "true", and the analytics module 432 proceeds to the next step.

In step 1416, using the poultry-piece: piece-type feature, validation occurs to ensure the correct piece type is being processed based on the batch specified. When the piece type with the highest score is not equivalent to the current piece type, step 1418 is performed. In step 1418, if the incorrect piece type is found or the piece type is unknown, then poultry-piece: decision-status feature is set to "re-evaluate" in step 1420 or "invalid" in step 1422 respectively. The analytics module 432 sends a message containing the piece-type features to the decision module 436 in step 1490. No other Analytics Pipeline Method image processing is performed for "invalid" or "reevaluated" identified pieces. For each image that is not "invalid" or "reevaluated" (poultry-piece: decision-status=true). a deep-learning object localization/detection model is invoked to extract the poultry-piece features: poultry-piece: perimeter-plot-coordinates and poultry-piece: piece-area-size features. These features will be used to create a mask 84 illustrated above, isolating the piece in the image so that the whole images no longer need to be analyzed.

In step 1416, when the piece type with the highest scores equal to the current piece type, step 1430 is performed. In step 1430, a piece mask is generated. There are many types of defects that may be analyzed for different types of pieces. In this example, a poultry piece is used. Some examples of the types of defects that may be detected in the present system and hair villi (filaments), rods (feathers), white and black root, inflammation, dermatitis, scabby, gore, decoloration such as yellow skin and a matter of cut. Each are examples of defects that may require remediation. Of course, the threshold for determining grade may be fixed or adjustable (an adjustable threshold). It may also be controlled by a governmental body. In some respects, the customer may be allowed to change the threshold at the user interface depending on the requirements of their client. Examples of defects to be remedied include hair size verification requirement examples, villi (filaments), single villi>0.5 cm, overall number of villi (5 or more): any size, a noticeable tufts/clusters of villi, rods that cannot exist of any size, white/black root, hair roots cannot exist of any size.

To identify a piece requiring remediation, a particular defect may be present or when compared to a threshold, is above the threshold. Inflammation may be an example of a defect, that when present, cause the piece to be a candidate for remediation. However, another way to determine a defect is in pieces with multiple defects. Each defect score could be weighted, and the overall score compared to a reject threshold to determine if the piece needs remediation. In one example, a small defect that alone would not trigger remediation, but may trigger remediation when found together with another small defect in one piece.

In step 1434, it is determined whether an image is available for edge analysis. Edge analysis is when the edge of the piece rather than the surface of the piece is determined. The edge of the piece may be highlighted with a high gain of the imaging devices. This is suitable for detecting filaments or villi and other types of defects. In step 1436, the image is filtered. In the filter image steps below and including 1436 the image may be augmented in a variety of way to enhance detection. In this example, an optical density filter may be used. For some type of defects, no filtering may be needed. In step 1438, the filaments or villi on the edge are determined. Step 1438 as well as the subsequent detection steps uses a deep learning object detection/localization model extracts the defect-candidate features found in the image.

All poultry-piece and defect-candidate features collected in step 1438 are added to an image marking message in step 1440 and wrapped with an analysis result message in step 1490. The image marking message may have defect specific data/numerical identifiers for each defect type. For filaments or villi, the villi edge defect type, the region subnode and the summary subnode may be included for each defect region found. The region subnode may include but is not limited to region area, perimeter, X/Y center coordinates, and plot points. The summary subnode may include max area, a count, area-sum, and an area sum raised to the nth power. All poultry-piece and defect-candidate features are sent to the decision module 436 instance for further processing in step 1492. All the data may be a numerical identifier for the part.

It should be noted that two images, one above the transparent belt and one from below the transparent belt, may be used in step 1438.

After steps 1434 through 1440, the surface defects may be classified in step 1442. That is, other types of defects on the surface of the piece are reviewed. Next a deep learning image classification model is invoked to classify the defect types found on the piece in step 1442. A list of found defect type(s) will be added to the poultry-piece: defects feature. For each defect listed, a specific deep-learning object localization/detection model is invoked. For each defect region identified by the model, two defect-candidate feature data will be generated: coordinates of the defect region location (defect-candidate: perimeter-plot-coordinates) and the area size (number of pixels) of the defect region (defect-candidate: area-size). Once all defect regions have been identified, additional defect candidate feature data are derived:

defect-candidate: max-area feature: created with the area size of the largest defect region found, defect-candidate: region-count feature that is the count of all the defect regions found, defect-candidate: area-sum feature, that is the sum of all the defect regions areas found, and defect-candidate: arean-sum feature is created with the sum of all area-size raised to the nth power for all defect regions found notated as $\Sigma_{i=1}^{n} a_i^x$, where $a_i^x$ is a derived defect area size a raised to a configurable x exponent for each defect i.

It should be noted that the use of the defect-candidate: area-size feature, particularly as a cumulative measure, is highly correlated with human (end customer) perception of defect significance, creating a useful method of determining a defect condition. By raising the defect-candidate area-size feature value to a specific power, a measure is created that aligns more closely with the human perspective that fewer larger defect has a disproportionately greater negative impact on quality perception than more numerous small defects.

In step 1443 when other types of defects are not present from step 1442, step 1490 is performed and an analysis result is obtained. In step 1443, when other types of defects are present, other defect types are analyzed. In step 1444, it is determined whether villi on the surface is present, and the characteristics of the surface villi are determined. The image may be filtered in step 1446. Villi defects are determined in step 1448 using the filtered image. Ultimately, in step 1450 an image marking message is generated that has a villi surface as the defect type, the region sub node, such as the region perimeter, the X/Y center of reference and various pilot points. Further a summary sub-node may be generated that has a count, an area sum, and an area sum raised to the nth power sum may be include in the image marking message data.

In step 1454, inflammation at the chicken piece is determined. For inflammation, dermatitis, scabbiness, gore, and yellow skin may be monitored. When inflammation is present (above an inflammation threshold), step 1456 is performed. In step 1456, the image is filtered or augmented as mentioned above. Inflammation defect data are determined in step 1458 using the filtered image with the classification described above. In step 1460, an image marking message having the inflammation defect type having the region sub node data and the summary sub node data for each region may all be determined.

In step 1464, when the rods or feathers are present (above a rod candidate threshold), step 1466 is performed. Rods are the end of a feather so the two can be used interchangeably. In step 1466, the image is filtered or augmented as mentioned above. In step 1468, the rod surface and rod edge defect data may be determined. In step 1470, an image marking message may be generated with a rod defect type, the region subnode data and the summary subnode data described above for each rod identified.

After step 1470, step 1474 is performed. Step 1474 presence of the matter of cut is determined by comparison to a matter of cut threshold. When the matter of cut is greater than the matter of cut threshold, step 1476 is performed in which the image is filter. In step 1478, the matter of cut data is detected. In step 1480, an image marking message may be generated that includes the region subnode data and the summary subnode data.

After step 1480, step 1482 is performed. In step 1482 when the root or feather class confidence not above a root candidate threshold, step 1490 is performed. When the root class confidence is above the root candidate threshold, step 1484 filters the image to filter out extraneous areas of the image. In step 1486, root surface and edge defects are determined for white root and black root. After step 1486, step 1488 generates an image marking message that provides the root or feather defect type, the region subnode data and the summary subnode data.

After step 1440, 1450, 1460, 1470, and 1480, step 1490 generates an analysis result that provides an image marking that is stored within the data base. These results are communicated to the decisioning module in step 1492.

Figure 15A:
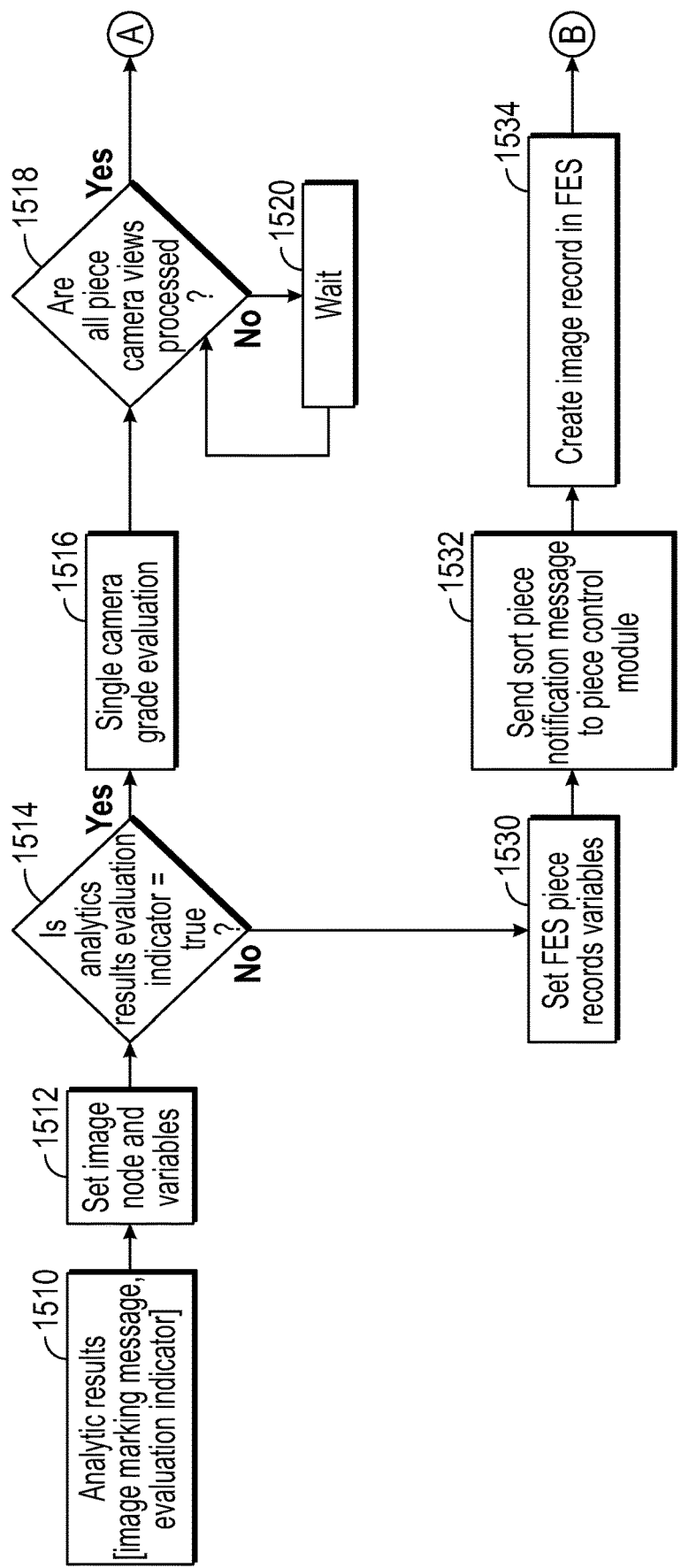
FIGS. 15A-15B is a flowchart for operating the decisioning module.
Figure 15B:
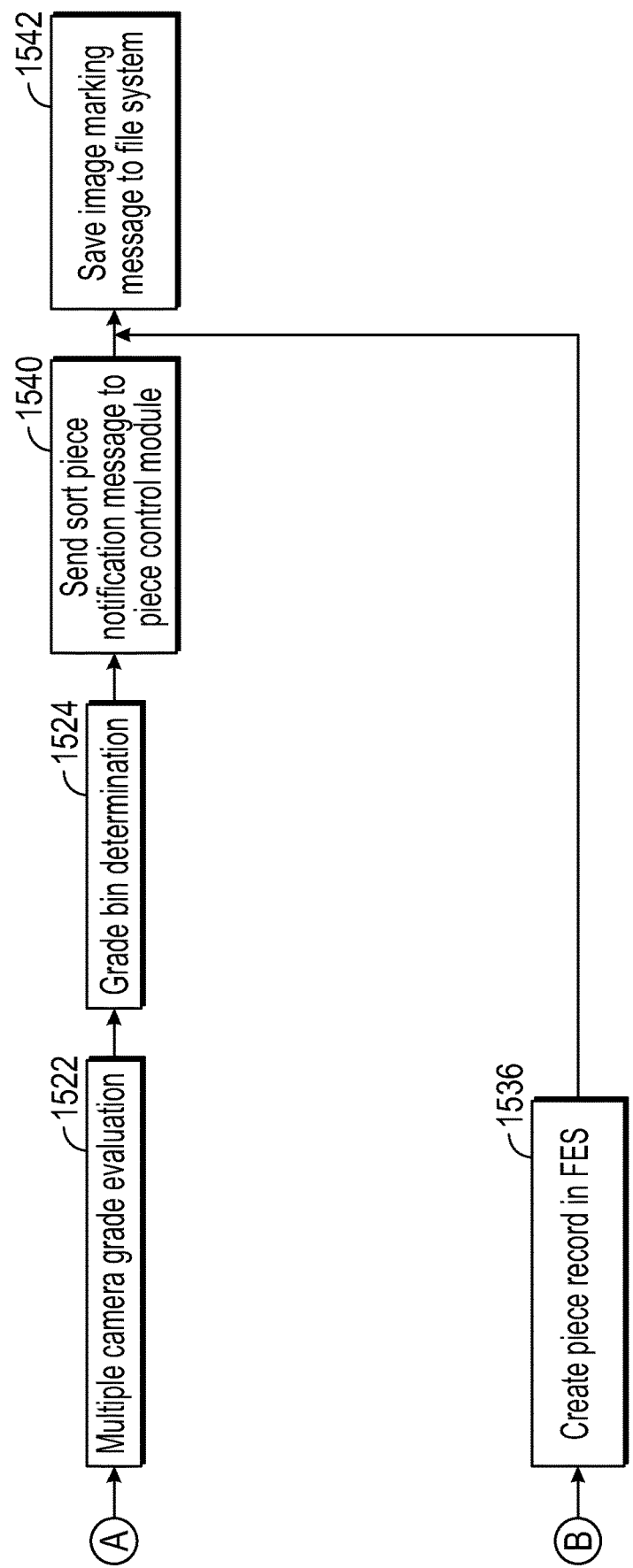

Referring now to FIGS. 15A and 15B, operation of the decisioning module 436 is set forth. The decisioning module 436 evaluates the results from the analyzing module 432 and determines the action that needs to take place such as determining the piece status, such as the grade, whether it is invalid or needs to be reevaluated. This is based on the image marking messages and the data contained therein generated in FIG. 14. Ultimately, the piece control module is used to perform the subsequent action. In step 1510, the image marking messages and the data therein are received from the analyzing module 432. As mentioned above, the results from the analyzing module 432 may include the image marking messages and an evaluation indicator to initiate evaluation of the data in the image marking messages.

In step 1512, the image marking message image node variables may be selected. The variables may include the image reference, the batch number, the piece type, the camera identifier and the encoder data. In step 1514, it is determined whether the analytics result evaluator indicator is true when the analytics results evaluation indicator is true, evaluation takes place which includes a single grade evaluation that is performed in step 1516. Details of this method will be described in more in FIG. 16. After step 1516, step 1518 determines whether all the piece camera views have been processed. If all the piece views have not been processed in step 1518, a wait time is step 1520 is performed. After step 1518, in step 1522, a multiple camera grade evaluation is performed. Details of the multi-camera grade evaluation is set forth below in FIG. 17. In step 1524, a grade bin determination is performed after step 1522. The grade bin evaluation is performed in FIG. 18.

In step 1514, when the analytics results evaluation indicator is not true, steps 1530 to 1536 are performed to bypass the grade evaluations and the grade bin determination. In step 1530, the FES piece record variables are set. A piece grade indicator may be set to no grade, a piece defect type may be set to an evaluation indicator. A grade bin indicator may be set to the value associated with the grade bin matrix using the piece defect type and the grade indicator. An image reference may be set to the location where the image resides. After step 1530, step 1532 a sort piece notification message may be sent to the piece control module 618. In step 1534, an image record may be created that has the record for the piece including the batch number, the encoder value, the camera identifier, the image reference, the piece type and an evaluation indicator. The image record is stored in the final evaluation structure (FES) image table which is indexed by the batch number and the encoder data. In step 1536, the piece record may also be saved in the FES piece table. Various types of data, such as the batch number, the encoder, the defect type, the grade bin, the image references, may all be stored in the piece table which is indexed by the batch number and the encoder data.

After step 1524 1536, step 1540 is performed. In step 1540, a sort piece notification message is sent to the piece control module 618. The sort piece notification message may include a batch number, encoder data and the remediation bin. After steps 1536 and step 1540, step 1542 may save in the file system the original image marking message received from the analyzing module 432. The image marking message may be indexed by the batch number, the encoder and the image reference number.

Figure 16A:
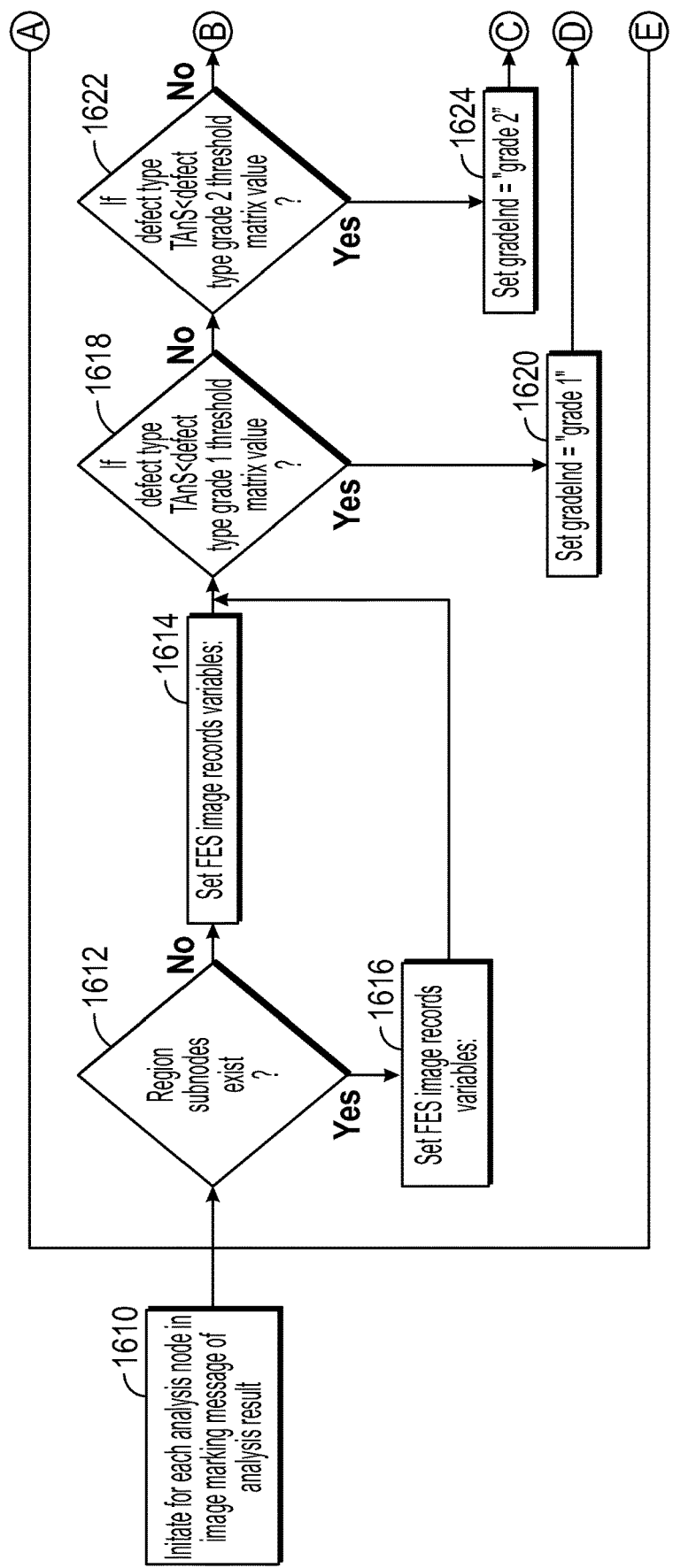
FIGS. 16A-16B is a flowchart of a method for operating the single camera grade evaluation of FIGS. 15A-15B.
Figure 16B:
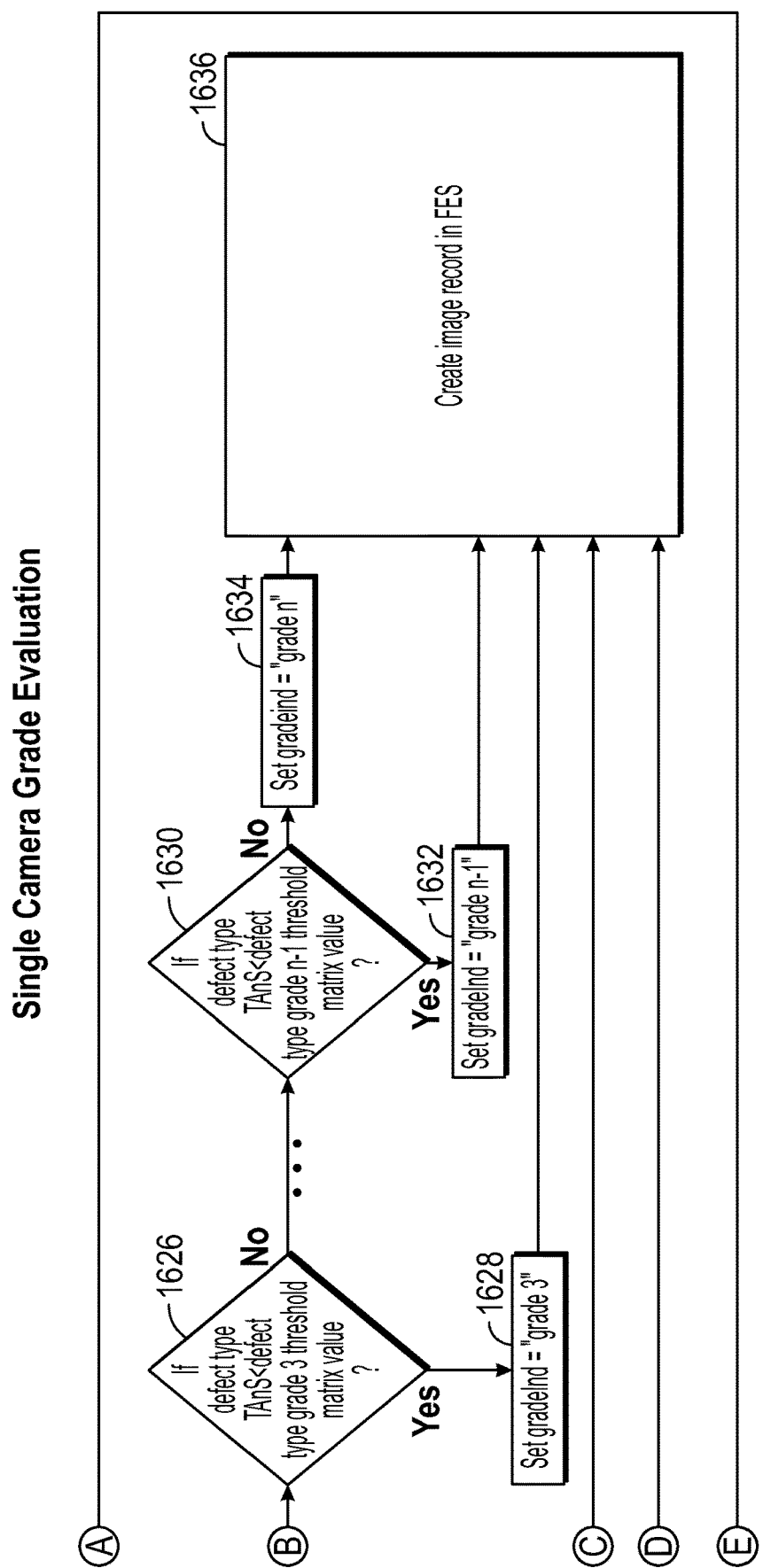

Referring now to FIGS. 16A and 16B, a method for performing the single camera grade evaluation (step 1516) in FIG. 15 is set forth. In step 1610, the single grade evaluation is initiated for each analysis node in the imaging marking message of the analysis result. In step 1612, it is determined whether subnodes exists. When subnodes do not exist, step 1614 is performed. No subnodes found correlates to no defects being found. Step 1614 sets the FES image record variables like max area, Total area, total area raised to the nth power and the region count to 0. In step 1612, when subnodes do exist, the 1616 is performed setting FES image record variables. Total area variable may be set to the sum of the region areas, total area to the nth power variable may be set to the sum of the region areas raised to the nth power, and region count variable may be set to the total number of regions found.

Figure 22:
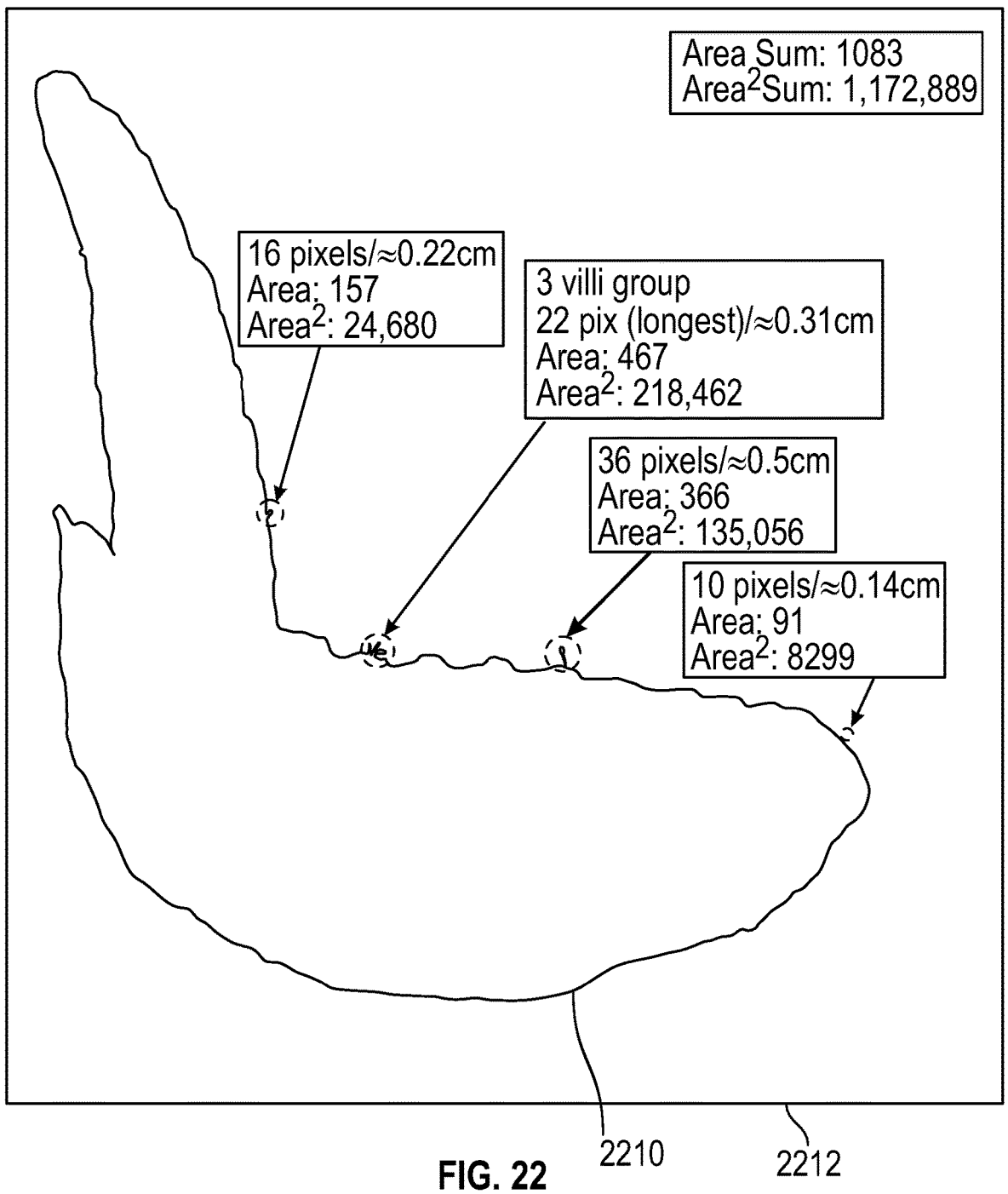
FIG. 22 is an image of a first chicken piece having edge filaments extending therefrom and coordinating data of the filament defect.

After steps 1614 and 1616, if the defect type is less than the defect type one grade threshold, step 1620 sets the grade equal to grade 1. The thresholds herein may be preset or may be set while running the batch from an input signal from the user interface. Each defect may have different characteristics for grading. For example, for filaments or villi, a physical 0.5 cm villi would appear with an approximate length of 36 pixels with a marked area of 365 for a defect score of 136,000 (as shown in FIG. 22 below). A villi cluster or group will typically present a marked area larger than that of a 0.5 cm villi (see FIG. 23). Further, 5 or more villi will present a defect score of 150,000 or greater. Based on this, if a piece has 5 or more villus and if there is at least one 0.5 cm villi a defect may be determined. Different sizes and amounts of villi may be used for the grading thresholds. This is done by the following approach:

Use defect count 5 or more from the analysis to determine if the 5 or more villi criteria has been met.

Use the largest defect region (max region) found from the analysis to determine if the 0.5+cm criteria or villi cluster has been met.

When this approach was used and ground truth was visually established, the solution achieved zero false negative (missed defects) and only 5% false positive rate (marked defect that were not defects).

After step 1618, when the defect type is less than the type two grade threshold in step 1622, the grade indicator is set to grade 2 in step 1624. After step 1622 and grade 2 is not found and when the grade defect is less than the grade three threshold matrix, the grade 3 threshold is set in step 1628. Various numbers of grades may be set and therefore the same logic may be applied to the various grade thresholds. Step 1630 indicates if the defect type is less than the defect type grade n-1 so that the grade is set when the defect type is less than the defect type threshold for the n-1 grade in step 1632. After step 1632, step 1634 sets the grade to grade n. After steps 1620, 1432, 1628, 1632 and 1634, step 1636 creates an image record in the FES system. The record may have the batch number, the encoder data, the grade indicator, the defect type, the max region area, the total area value, the total sum of the region areas raised to the nth power value, the region count value, the camera identifier, an image reference, a piece type, an evaluation indicator as well as the image table index by the batch number and encoder data.

Figure 17A:
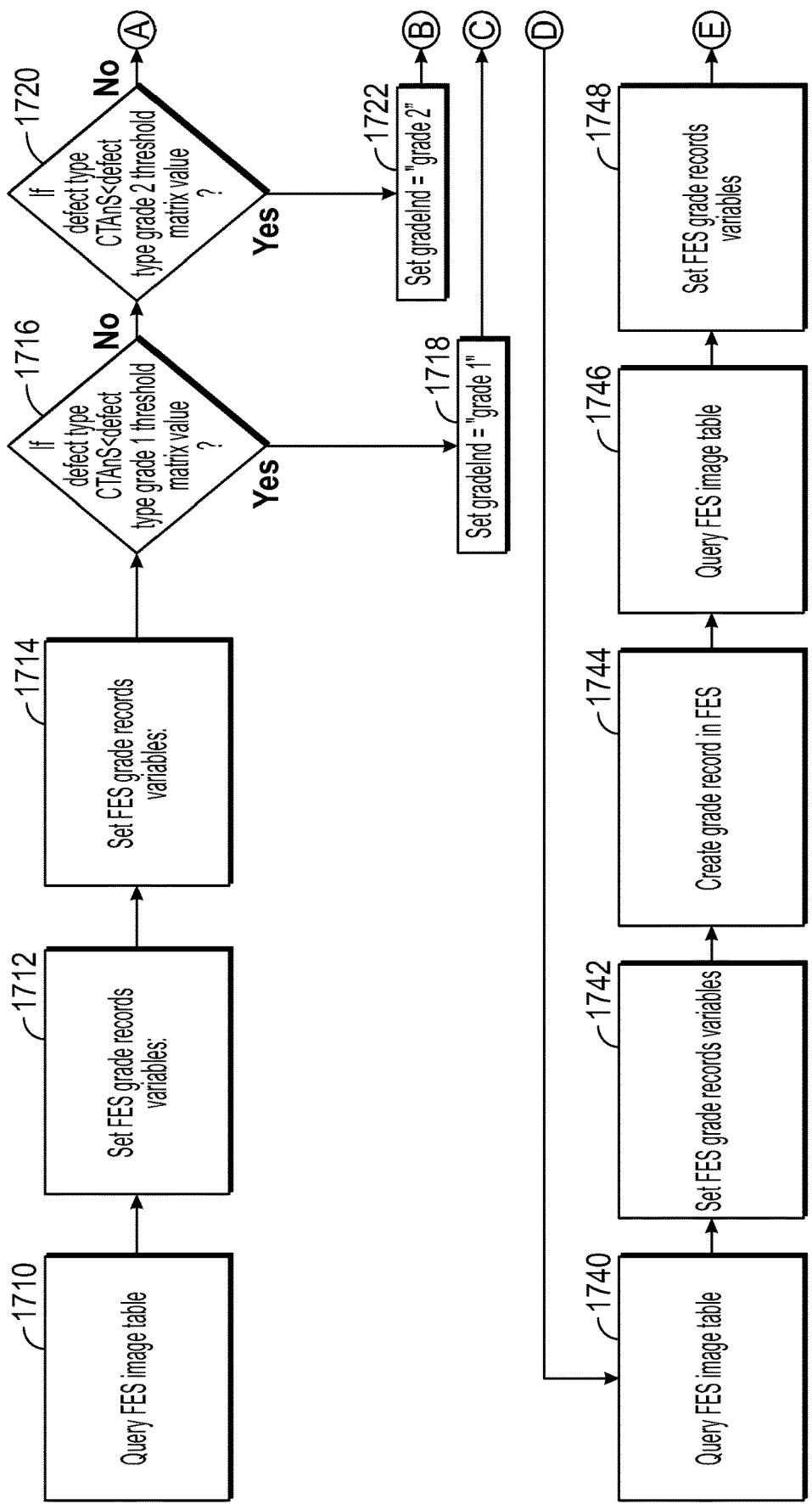

Referring now to FIGS. 17A and 17B, details of the multiple camera grade evaluation step 1522 in FIG. 15 is set forth. In this example, the FES image table is queried. The FES image table is used to select the row where the batch number, the encoder data and the current defect type is filaments or villi edge OR filaments or villi surface in step 1710. In step 1712, the FES grade record variables are set. Step 1712 looks at the villi edge defect type records and selects the record with the largest total of region areas raised to the nth power value. The variable CTAnS is set to the total of region areas raised to the nth power value of the selected record. The image reference 1 variable is set to the image location reference of the selected record. The variable CTAS is set to the total region areas of the selected record. Step 1714 looks at the villi surface defect type records and selects the record with the largest total of region areas raised to the nth power value. The total of region areas raised to the nth power value of the selected record is added to the CTAnS variable. The image reference 2 variable is set to image location reference of the selected record. The total of region areas value of the select record is added to the CTAS variable. In step 1716, the CTAnS value is compared to a grade 1 threshold when the defect type CTAnS is less than the defect grade 1 threshold, step 1718 sets the grade equal to 1. In step 1720, the CTAnS is compared to the grade 2 threshold matrix value. When the defect type CTAnS is less than the grade 2 threshold matrix value, step 1722 sets the grade to grade 2. After step 1720, the \ CTAnS is compared to a defect type 3 threshold matrix value. In step 1726, the threshold of grade 3 is set when the defect type CTAnS is less than the grade 3 threshold value. The comparison continues in steps 1728 and 1730 which are performed for n-1 grade. That is, various numbers of grades may be represented in this method. Steps 1728 sets the n-1 grade when the CTAnS is less than the defect type grade n-1. Grade n is set in steps 1732. After step 1718, 1722, 1726, 1730 and 1732, the grade record is created in the final evaluation structure (FES). The batch number, encoder type, the grade indicator, the defect type, such as villi or a filament, as well as the batch number and encoder data are all saved in the table.

Steps 1710 through 1734 are performed for filaments or villi. Other detection may be performed at indicated merely upon their presence or a comparison to a threshold. In the first non-filament example, inflammation is detected. In step 1740, a query may be made to the image table. In step 1740, the FES image table rows where the batch number and encoder values are set to current, and the defect type is set to inflammation. In step 1742, the FES grade record variables are set from values of the record with the largest total of region areas raised to the nth power value. The grade indicator, the total of region areas raised to the nth power, total of region area, and the image reference 1 variables are all set from the associated values of the selected record. In step 1744, a grade record is created in the final evaluation structure. The record is saved with the batch number, the encoder data, the grade indicator, the defect type, total of region areas raised to the nth power, total of region area, and image reference 1 information which is indexed by the batch number and encoder type.

The next defect is the presence of a rod. In step 1746, the FES image table is query. The FES image table rows where the batch number and encoder key values are set to the current and the defect type is set to a rod. In step 1748, the FES grade record variables are set from values of the record with the largest total of region areas raised to the nth power value. The grade indicator, the total of region areas raised to the nth power, total of region area, and the image reference 1 variables are all set from the associated values of the selected record. In step 1750, the FES grade record is saved with the batch number, the encoder data, the grade indicator, the defect type, total of region areas raised to the nth power, total of region area, and image reference 1 information and the final evaluation structure coordinated by the batch number and encoder data. In step 1752 and 1754, the same is performed for a root or feathers type of defect. In step 1752, a query is performed for the FES image table. In this example, the rows where the batch number and the encoder key value are set to the current batch number and the defect type is set as the root or feathers. In step 1754, the FES grade record variables are set from values of the record with the largest total of region areas raised to the nth power value. The grade indicator, the total of region areas raised to the nth power, total of region area, and the image reference 1 variables are all set from the associated values of the selected record. In step 1756, the FES grade record is saved with the batch number, the encoder data, the grade indicator, the defect type, total of region areas raised to the nth power, total of region area, and image reference 1 information and the final evaluation structure coordinated by the batch number and encoder data.

Figure 18:
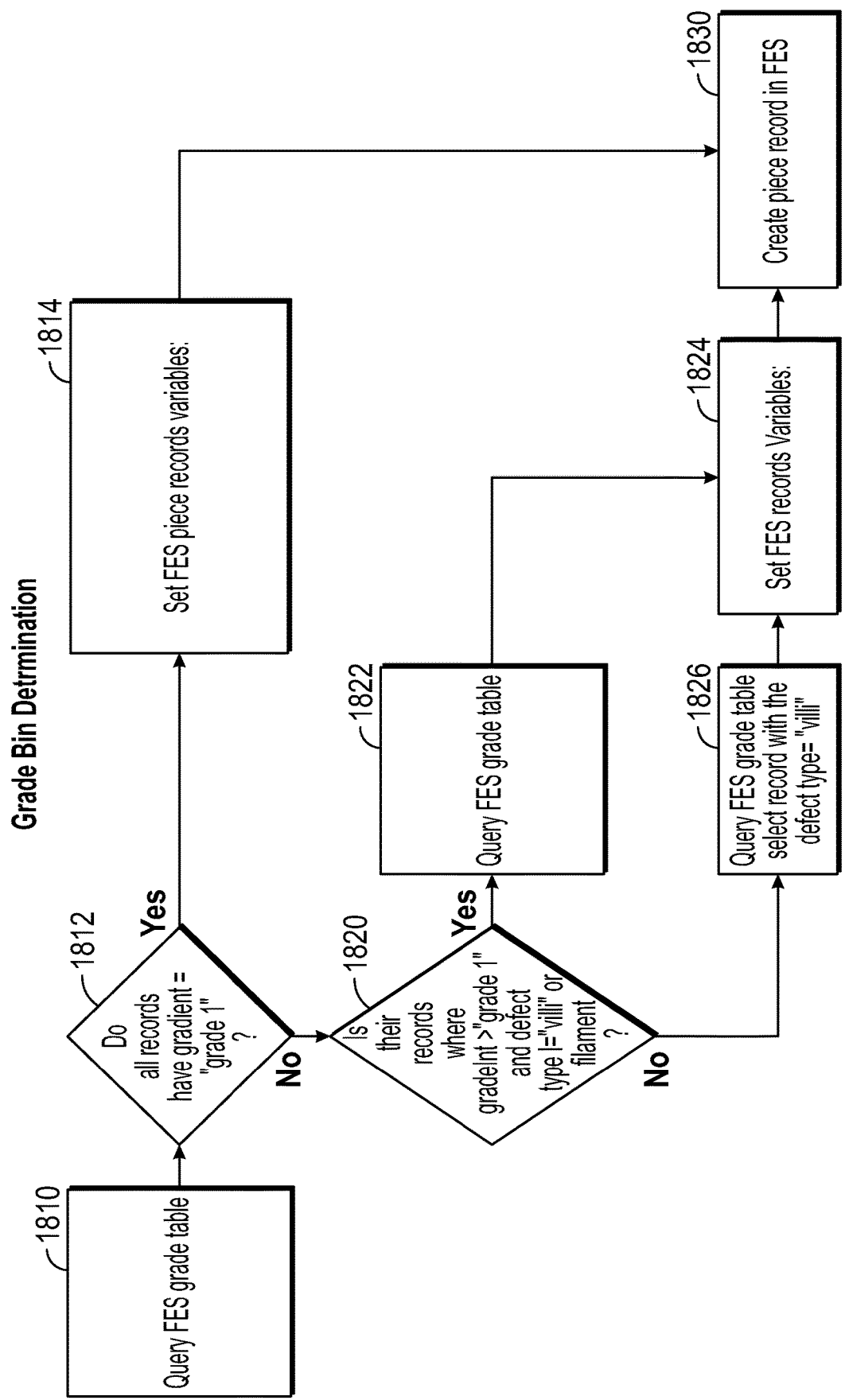
FIG. 18 is a flowchart of the grade bin determination of FIG. 1.

Referring now to FIG. 18, the grade bin determination step 1524 of FIG. 15 is set forth in further detail. In this example, a query for FES grade table is performed. The final evaluation grade table rows are selected for the batch number and the encoder value being the current value in step 1810. This coordinates to the particular piece being evaluated. In step 1812, when all the records for the defects have a grade of one, step 1814 is performed. In step 1814, the FES piece records variables are set such as the grade is equal to 1, no defects are found and the like. Referring to step 1812, when the grade records are not all grade 1, step 1820 is performed. In step 1820, if the records have a grade value greater than 1 and the defect type is not villi or filament, step 1822 is performed. In step 1822, a query is performed at the FES grade table to select the record type with the highest defect type with the highest remediation precedent based on the grade bin matrix. Thereafter, step 1824 sets the FES piece record variables. In step 1820, when the record is greater than grade 1 and the defect type is villi, step 1826 a query of the FES grade table is performed. In step 1826, the record type of villi is selected. Step 1824 is performed after steps 1822 and 1826. As mentioned above, the FES piece records variables are set. The grade is set to the record grade, the defect is set to the defect type and the grade bin is set accordingly. After step 1824 or after step 1814, step 1830 creates a piece record in the final evaluation structure.

Referring now to FIG. 19, a grade threshold matrix example is set forth. The grade threshold matrix is illustrated and are set with rows corresponding to various types of defects such as the filament edge, the filament surface, inflammation, rods, feathers and roots. Each of the defect types has a row with numbers corresponding to various grades.

Referring now to FIG. 20, a grade bin matrix 2010 determined in FIG. 18 is set forth. FIG. 20 assess all the defect types associated to a piece and assigns the grade associated with the highest priority defect type based on an established defect type precedence and associates a grade bin to the piece based on the assigned grade using a pre-determined Grade Bin Matrix. Even pieces of defect type of "invalid" or "Reevaluate" are assigned a grade bin number. The grade bin matrix has various defect types that correspond to the rows and several columns including a defect precedents column, a no grade column, a grade 1 column, a grade 2 column, a grade 3 column and a grade 4 column, of course, n-1 and n may be provide in the columns to indicate that various numbers of defects may be determined by the system. Various numbers are provided in the various rows.

Figure 21:
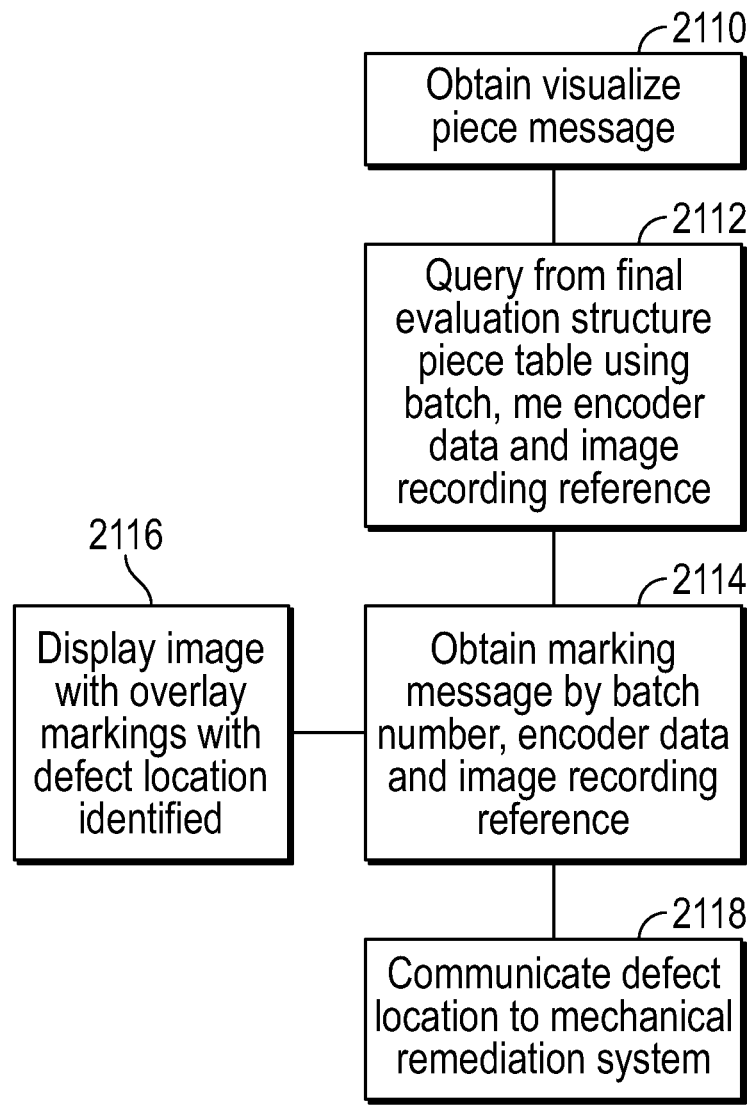
FIG. 21 is a flowchart of a method for operating the visualized and robotic piece enablement module.

Referring now to FIG. 21, the visualize/automated piece enablement module 628 is illustrated in further detail. In this example, the visualize/mechanical remediation enablement module 628 is used to visualize the piece with the defect on the display 30 of the manual remediation system 28A. Automated remediation may also be provided in which a display is not required and the coordinates area and the like corresponding to the defect are set forth. In step 2110, a visualized piece message is obtained. In step 2112, a query of the FES piece table for the database matching the batch number and encoder data is used to obtain the image desired. The marking message is obtained in step 2114 by batch number, encoder data and the image recording reference. Ultimately, the image and the defect position and area are provided to a display which, in step 2116, displays the image with the overlay markings with the defect location identified. This is performed for a manual remediation system. After step 2114, if automated or mechanical remediation is to be performed, step 2118 provides the coordinates and the data so that the automated remediation system or mechanical means can remediate the defect Referring now to FIG. 22, an image 2210 of a chicken piece within a field of view 2212 is shown. In this example, the image of the chicken piece has four areas that have an area outlined thereon. The area outlined corresponds to the severity of the filaments or villus extending from the piece 2210. In the first example, 16 pixels or 0.22 cm is obtained. An area of 157 is therefore obtained which squares to 2468. The second example provides 36 pixels, which is approximately 0.5 cm. The area is 366 and the area squared is 135,056. In the third example, ten pixels corresponds to 0.14 cm for the area of the filaments. The area is 91 and the area is 8299. In a fourth example, the area of 21 pixels corresponds to several villi or filaments in a cluster. Three villi are found in this sample. The area sum of the four areas is 1083 while the area sum to the nth power (2 in this example) is 1,172,889. These sums may be added and provided along with the data to show the area sum which is 616 and the area squared sum which is 168,036. Each of these points of data may be used individually or together to determine the grade and defect analysis.

Figure 23:
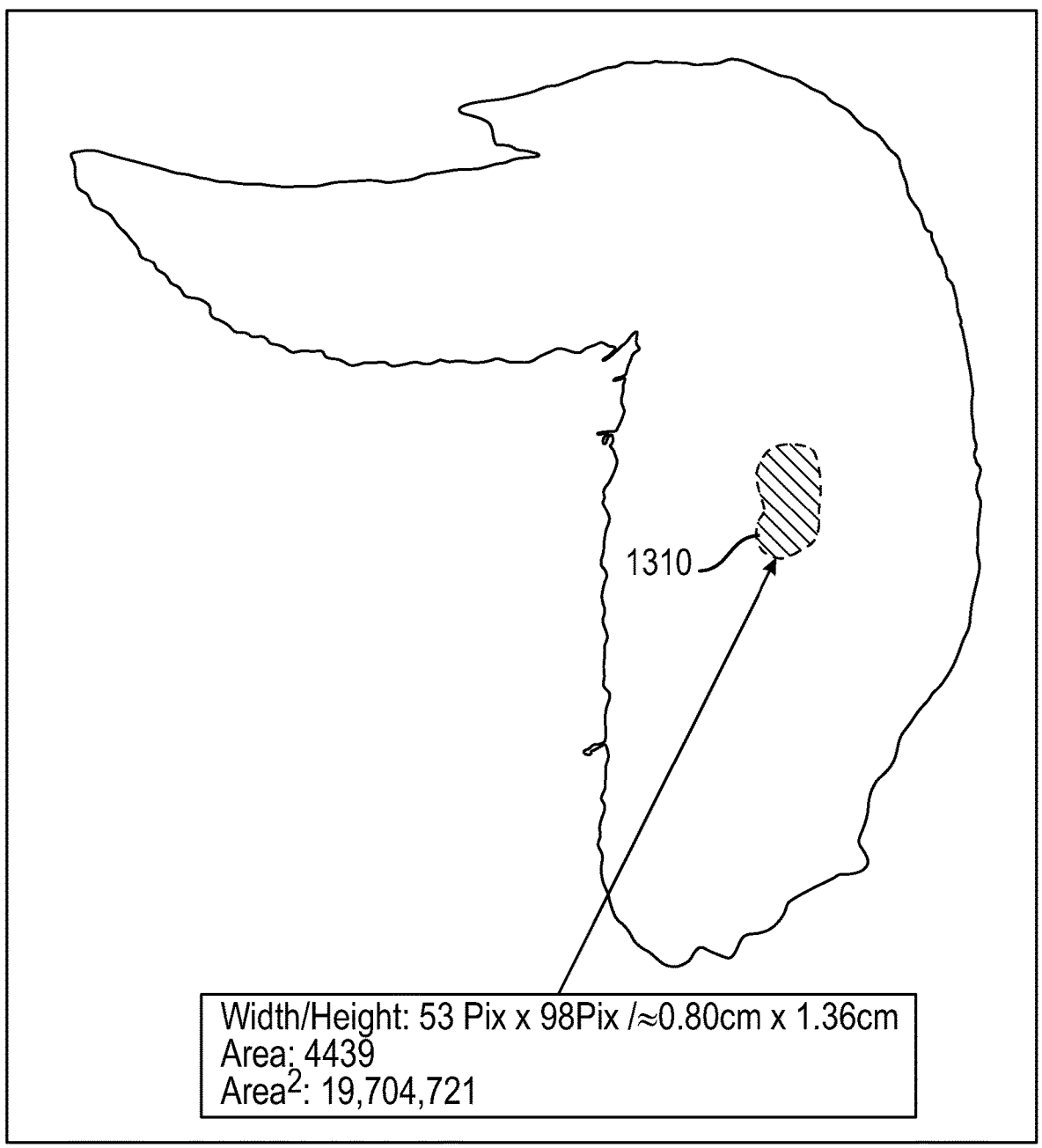
FIG. 23 is an image of a second chicken piece having a surface defect thereon.

Referring now to FIG. 23, a surface defect area 1310 is illustrated on a chicken piece. In this example, the defect area may represent surface filaments or villi, inflammation defects (dermatitis, scabby, gore, and yellow skin), decolorization, feather/rods, white root and black roots and a matter of cut. The identified area is about 53 pixels by 98 pixels which corresponds to about 0.8 cm by 1.36 cm. The area corresponds to 4439 which is 19,704,721.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of inspecting a chicken piece comprising:
generating an image for the chicken piece by generating a first image for a first side of the chicken piece with a first image device using a first gain, a second image for a second side of the chicken piece with a second image device using a second gain, a third image for the first side of the chicken piece with a third image device using a third gain and a fourth image for the second side of the chicken piece with a fourth image device using a fourth gain, said first gain different than the third gain and the second gain is different than the fourth gain;
identifying a defect type, a defect location and an area of each defect on the chicken piece based on the image; and
grading the chicken piece into a grade of a plurality of grades based on the defect type and the area.

2. The method of claim 1 wherein generating the image comprises generating the image from within an enclosure.

3. The method of claim 1 wherein generating the image comprises generating the image when the chicken piece enters a field of view of an image device.

4. The method of claim 1 wherein generating the image comprises generating a first image for a first side of the chicken piece and a second image for a second side of the chicken piece.

5. The method of claim 1 wherein generating the image comprises generating a first image for a first side of the chicken piece and generating a second image for a second side of the chicken piece through a transparent conveyor belt.

6. The method of claim 5 wherein prior to generating a second image for the second side of the chicken piece through the transparent conveyor belt, cleaning the transparent belt.

7. The method of claim 1 wherein generating the image comprises generating a first image for a first side of the chicken piece, a second image for a second side of the chicken piece, a third image for the first side of the chicken piece and a fourth image for the second side of the chicken piece.

8. The method of claim 1 wherein identifying the defect type, the defect location and the area of each defect on the chicken piece comprises identifying the defect type, the defect location and the area of each defect on the chicken piece using deep learning image classification and deep learning object detection.

9. The method of claim 1 further comprising sorting the chicken piece in a sorting system based on the grade.

10. The method of claim 1 further comprising communicating the chicken piece from a sorting system to a remediation system based on the grade.

11. The method of claim 1 further comprising determining a piece type based on the image.

12. The method of claim 11 further comprising sorting the piece in a sorting system based on the grade and piece type.

13. The method of claim 1 further comprising displaying on a display the image and the defect location.

14. The method of claim 1 wherein identifying the defect type comprises determining areas of a plurality of defects and summing the areas.

15. The method of claim 1 wherein identifying the defect type comprises determining a filament or a cluster of filaments.

16. The method of claim 1 wherein identifying the defect type comprises determining at least one of a dermatitis, scabby, and gore.

17. The method of claim 1 wherein identifying the defect type comprises determining decolorization.

18. The method of claim 1 wherein identifying the defect type comprises determining rods or feathers.

19. The method of claim 1 wherein identifying the defect type comprises determining white roots or black roots.

20. The method of claim 1 wherein identifying the defect type comprises determining a matter of cut.

21. The method of claim 1 wherein identifying the defect type is based on an adjustable threshold.

22. A method of inspecting a chicken piece comprising:
generating an image for the chicken piece;
identifying a defect type, a defect location and an area of each defect on the chicken piece based on the image by determining an area of a defect raised to an exponent; and
grading the chicken piece into a grade of a plurality of grades based on the defect type and the area.

23. The method of claim 22 wherein generating the image comprises generating the image from within an enclosure.

24. The method of claim 22 wherein generating the image comprises generating the image when the chicken piece enters a field of view of an image device.

25. The method of claim 22 wherein generating the image comprises generating a first image for a first side of the chicken piece and a second image for a second side of the chicken piece.

26. The method of claim 22 wherein generating the image comprises generating a first image for a first side of the chicken piece and generating a second image for a second side of the chicken piece through a transparent conveyor belt.

27. The method of claim 26 wherein prior to generating a second image for the second side of the chicken piece through the transparent conveyor belt, cleaning the transparent belt.

28. The method of claim 22 wherein generating the image comprises generating a first image for a first side of the chicken piece, a second image for a second side of the chicken piece, a third image for the first side of the chicken piece and a fourth image for the second side of the chicken piece.

29. The method of claim 22 wherein identifying the defect type, the defect location and the area of each defect on the chicken piece comprises identifying the defect type, the defect location and the area of each defect on the chicken piece using deep learning image classification and deep learning object detection.

30. The method of claim 22 further comprising sorting the chicken piece in a sorting system based on the grade.

31. The method of claim 22 further comprising communicating the chicken piece from a sorting system to a remediation system based on the grade.

32. The method of claim 22 further comprising determining a piece type based on the image.

33. The method of claim 32 further comprising sorting the piece in a sorting system based on the grade and piece type.

34. The method of claim 22 further comprising displaying on a display the image and the defect location.

35. The method of claim 22 wherein identifying the defect type comprises determining areas of a plurality of defects and summing the areas.

36. The method of claim 22 wherein identifying the defect type comprises determining at least one of a filament, a cluster of filaments, dermatitis, scabby, and gore, decolorization, rods, feathers white roots, black roots and a matter of cut filament or a cluster of filaments.

37. The method of claim 22 wherein identifying the defect type is based on an adjustable threshold.

38. An inspection system for inspecting an item comprising:
a conveyor belt for moving the item thereon;
a first image device generating a first image signal of the item from a first field of view;
a second image device generating a second image signal of the item from a second field of view;
a third image device generating a third image signal of the item from a third field of view;
a fourth image device generating a fourth image signal from a fourth field of view;
an electromagnetic source disposed within the enclosure directing electromagnetic radiation to the first field of view and the second field of view;
a controller coupled to the first image device, the second image device, the third image device and the fourth image device, said controller generating a numerical identifier based on the first image signal, the second image signal, the third image signal and the fourth image signal; and
a display displaying an indicator based on the numerical identifier.

39. The inspection system of claim 38 further comprising an enclosure disposed around the first field of view and the second field of view.

40. The inspection system of claim 38 wherein the conveyor comprises a transparent conveyor belt and wherein first image device is disposed on a first side of the conveyor belt and the second image device is disposed on a second first side of the conveyor belt.

41. The inspection system of claim 40 further comprising a cleaning system cleaning the transparent conveyor belt.

42. The inspection system of claim 38 wherein the first field of view is aligned with the second field of view.

43. The inspection system of claim 38 wherein the electromagnetic source comprises a first portion disposed on a first side of the conveyor belt and a second portion disposed on a second side of the conveyor belt.

44. The inspection system of claim 41 wherein the cleaning system comprises an air knife and a bath.

45. The inspection system of claim 38 wherein the first image device comprises a first gain and the second image device comprises a second gain different that the second gain.

46. The inspection system of claim 38 wherein the second field of view is spaced apart from the first field of view.

47. The inspection system of claim 38 wherein the second image device and the fourth image device are disposed on opposite sides of the conveyor belt as the first image device and the third image device, the first field is aligned with the second field of view and the third field of view is aligned with the fourth field of view.

48. The inspection system of claim 38 further comprising a sorting system sorting the item based on the numerical identifier.

49. The inspection system of claim 38 wherein the controller determines the numerical identifier by determining an area of a defect.

50. The inspection system of claim 38 wherein the controller determines the numerical identifier by determining areas of a plurality of defects and summing the areas to form the numerical identifier.

51. The inspection system of claim 38 wherein the item comprises a poultry piece and wherein the numerical identifier comprises a surface defect.

52. The inspection system of claim 51 wherein the surface defect comprises a filament and cluster of filaments.

53. The inspection system of claim 51 wherein the surface defect comprises at least one of a dermatitis, scabby, and gore.

54. The inspection system of claim 51 wherein the surface defect comprises decolorization.

55. The inspection system of claim 51 wherein the surface defect comprises rods or feathers.

56. The inspection system of claim 51 wherein the surface defect comprises white roots or black roots.

57. The inspection system of claim 51 wherein the surface defect comprises a matter of cut.

58. The inspection system of claim 38 wherein the electromagnetic source comprises a visible light system.

59. The inspection system of claim 38 further comprising a display device coupled to the controller, said display device generating an image of the item and display indicia identifying a surface defect.

60. The inspection system of claim 38 wherein the numerical identifier comprises a grade of a plurality of grades.

61. The inspection system of claim 60 wherein the grade corresponds to a plurality of thresholds adjustable using a user interface.

62. The inspection system of claim 38 wherein the controller comprises a deep learning image classifier and deep learning object detection.

63. An inspection system for inspecting an item comprising:
a conveyor belt for moving the item thereon;
a first image device generating a first image signal of the item from a first field of view;
a second image device generating a second image signal of the item from a second field of view;
an electromagnetic source disposed within the enclosure directing electromagnetic radiation to the first field of view and the second field of view; and
a controller coupled to the first image device and the second image device generating a numerical identifier based on the first image signal and the second image signal and by determining an area of a defect raised to an exponent; and
a display displaying an indicator based on the numerical identifier.

64. The inspection system of claim 63 further comprising a user interface for changing the exponent.

65. The inspection system of claim 63 further comprising an enclosure disposed around the first field of view and the second field of view.

66. The inspection system of claim 63 wherein the conveyor comprises a transparent conveyor belt and wherein first image device is disposed on a first side of the conveyor belt and the second image device is disposed on a second first side of the conveyor belt.

67. The inspection system of claim 66 further comprising a cleaning system cleaning the transparent conveyor belt.

68. The inspection system of claim 63 wherein the first field of view is aligned with the second field of view.

69. The inspection system of claim 63 wherein the electromagnetic source comprises a first portion disposed on a first side of the conveyor belt and a second portion disposed on a second side of the conveyor belt.

70. The inspection system of claim 67 wherein the cleaning system comprises an air knife and a bath.

71. The inspection system of claim 63 wherein the first image device comprises a first gain and the second image device comprises a second gain different that the second gain.

72. The inspection system of claim 63 wherein the second field of view is spaced apart from the first field of view.

73. The inspection system of claim 63 further comprising a sorting system sorting the item based on the numerical identifier.

74. The inspection system of claim 63 wherein the controller determines the numerical identifier by determining an area of a defect.

75. The inspection system of claim 63 wherein the controller determines the numerical identifier by determining areas of a plurality of defects and summing the areas to form the numerical identifier.

76. The inspection system of claim 63 wherein the item comprises a poultry piece and wherein the numerical identifier comprises a surface defect.

77. The inspection system of claim 76 wherein the surface defect comprises at least one of a filament, a cluster of filaments, dermatitis, scabby, and gore, decolorization, rods, feathers white roots, black roots and a matter of cut.

78. The inspection system of claim 63 wherein the electromagnetic source comprises a visible light system.

79. The inspection system of claim 63 further comprising a display device coupled to the controller, said display device generating an image of the item and display indicia identifying a surface defect.

80. The inspection system of claim 63 wherein the numerical identifier comprises a grade of a plurality of grades.

81. The inspection system of claim 80 wherein the grade corresponds to a plurality of thresholds adjustable using a user interface.

82. The inspection system of claim 63 wherein the controller comprises a deep learning image classifier and deep learning object detection.

* * * * *